(12) United States Patent
Sandell et al.

(10) Patent No.: US 8,435,937 B2
(45) Date of Patent: *May 7, 2013

(54) INHIBITION OF MIGRATION AND INDUCTION OF CELL DEATH BY THE TYPE II COLLAGEN AMINO PROPEPTIDES

(75) Inventors: Linda Sandell, St. Louis, MO (US); Zhepeng Wang, Ballwin, MO (US)

(73) Assignee: Washington University, St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 13/442,352

(22) Filed: Apr. 9, 2012

(65) Prior Publication Data
US 2012/0196364 A1 Aug. 2, 2012

Related U.S. Application Data

(62) Division of application No. 12/836,832, filed on Jul. 15, 2010, now Pat. No. 8,278,266, which is a division of application No. 12/098,942, filed on Apr. 7, 2008, now Pat. No. 7,851, 436.

(60) Provisional application No. 60/910,361, filed on Apr. 5, 2007.

(51) Int. Cl.
*A61K 38/00* (2006.01)

(52) U.S. Cl.
USPC .......................................................... 514/1.1

(58) Field of Classification Search .................. None
See application file for complete search history.

(56) References Cited

U.S. PATENT DOCUMENTS 5,399,347 A * 3/1995 Trentham et al. .......... 424/184.1
5,466,468 A 11/1995 Schneider

OTHER PUBLICATIONS

Notice of Allowance dated Apr. 15, 2010 from related U.S. Appl. No. 12/098,942, 7 pgs.
Achilefu et al, Synergistic effects of light-emitting probes and peptides for targeting and monitoring integrin expression, PNAS, 2005, pp. 7976-7981, vol. 102, No. 22.
Ackley et al, Oligomerization-dependent Regulation of Motility and Morphogenesis by the Collagen XVIII NC1/Endostatin Domain, J. Cell Biology, 2001, pp. 1233-1246, vol. 152, No. 6.
Altschul et al, Basic Local Alignment Search Tool, J. Mol. Biol., 1990, pp. 403-410, vol. 215.
Altschul et al, Gapped BLAST and PSI-BLAST: a new generation of protein database search programs, Nucleic Acids Research, 1997, pp. 3389-3402, vol. 25, No. 17.
Brem et al, Inhibition of Tumor Angiogenesis Mediated by Cartilage, J. of Exp. Med., 1975, pp. 427-439, vol. 141.
Brooks et al, Integrin αvβ3 Antagonists Promote Tumor Regression by Inducing Apoptosis of Angiogenic Blood Vessels, Cell, 1994, pp. 1157-1164, vol. 79.
Chansky et al, Expression of Cartilage Extracellular Matrix and Potential Regulatory Genes in a New Human Chondrosarcoma Cell Line, J. Orthop. Res., 1998, pp. 521-530, vol. 16, No. 5.
Darland et al, Blood vessel maturation: vascular development comes of age, J. Clin. Invest., 1999, pp. 157-158, vol. 103, No. 2.
Dell et al, The Role of PDGF Receptor Inhibitors and PI3-Kinase Signaling in the Pathogenesis of Corneal Neovascularization, Invest. Ophthalmol. Vis. Sci., 2006, pp. 1928-1937, vol. 47.
Eisenstein et al, The Resistance of Certain Tissues to Invasion, Am. J. Pathol., 1973, pp. 765-774, vol. 73.
Friedlander et al, Involvement of integrins αvβ3 and αvβ5 in ocular neovascular diseases, PNAS, 1996, pp. 9764-9769, vol. 93.
Hayami et al, Specific loss of chondromodulin-I gene expression in chondrosarcoma and the suppression of tumor angiogenesis and growth by its recombinant protein in vivo, FEBS Letters, 1999, pp. 436-440, vol. 458.
Karlin et al, Methods for assessing the statistical significance of molecular sequence features by using general scoring schemes, PNAS, pp. 2264-2268, vol. 87, 1990.
Kenyon et al, A Model of Angiogenesis in the Mouse Cornea, Invest. Ophthalmol. Vis. Sci., 1996, pp. 1625-1632, vol. 37, No. 8.
Kruger et al, Protein Binding Alters the Activity of Suramin, Carboxyamidotriazole, and UCN-01 in an ex Vivo Rat Aortic Ring Angiogenesis Assay, Clin. Can. Res., 2001, pp. 1867-1872, vol. 7.
Kusafuka et al, Cartilage-specific matrix protein, condromodulin-I (ChM-I), is a strong angio-inhibitor in endochondral ossification of human neonatal vertebral tissues in vivo: relationship with angiogenic factors in the cartilage, ACTA Histochem., 2002, pp. 167-175, vol. 104, No. 2.
Kyriakides et al, The Distribution of the Matricellular Protein Thrombospondin 2 in Tissues of Embryonic and Adult Mice, J. Histochem. Cytochem., 1998, pp. 1007-1015, vol. 46, No. 9.
Langer et al, Isolation of a Cartilage Factor That Inhibits Tumor Neovascularization, Science, pp. 70-71, vol. 193, 1976.
Maeshima et al, Tumstatin, an Endothelial Cell-Specific Inhibitor of Protein Synthesis, Science, 2002, pp. 140-143, vol. 295.
Maubant et al, Blockade of αvβ3 and αvβ5 integrins by RGD mimetics induces anoikis and not integrin-mediated death in human endothelial cells, Blood, pp. 3035-3044, vol. 108, 2006.
McAlinden et al, α-Helical Coiled-coil Oligomerization Domains Are Almost Ubiquitous in the Collagen Superfamily, J. Biol. Chem., 2003, pp. 42200-42207, vol. 278, No. 43.
McAlinden et al, Trimerization of the Amino Propeptide of Type IIA Procollagen Using a 14-Amino Acid Sequence Derived from the Coiled-Coil Neck Domain of Surfactant Protein D, J. Biol. Chem., 2002, pp. 41274-41281, vol. 277, No. 43.
Moses et al, Troponin I is present in human cartilage and inhibits angiogenesis, PNAS, 1999, pp. 2645-2650, vol. 96.
Nyberg et al, Endogenous Inhibitors of Angiogenesis, Cancer Res., 2005, pp. 3967-3979, vol. 65, No. 10.

(Continued)

*Primary Examiner* — Laura B Goddard
(74) *Attorney, Agent, or Firm* — Polsinelli Shughart PC

(57) ABSTRACT

The present invention provides combinations and methods for inducing cell death, inhibiting angiogenesis, and inhibiting cell migration. In particular, the present invention provides methods for inducing cell death in a cell expressing an αvβ3 and/or an αvβ5 integrin.

5 Claims, 24 Drawing Sheets
(10 of 24 Drawing Sheet(s) Filed in Color)

OTHER PUBLICATIONS

Oganesian et al, Type IIA Procollagen Amino Propeptide Is Localized in Human Embryonic Tissues, J. Histochem. Cytochem., 1997, pp. 1469-1480, vol. 45, No. 11.

Passaniti et al, A Simple, Quantitative Method for Assessing Angiogenesis and Antiangiogenic Agents Using Reconstituted Basement Membrane, Heparin, and Fibroblast Growth Factor, Laboratory Investigation, 1992, pp. 519-528, vol. 67, No. 4.

Prockop et al, Procollagen N-Proteinase and Procollagen C-Proteinase. Two Unusual Metalloproteinases that are Essential for Procollagen Processing Probably Have Important Roles in Development and Cell Signaling, Matrix Biology, 1997, pp. 399-408, vol. 16.

Reardon et al, Localization of pN-type IIA procollagen on adult bovine vitreous collagen fibrils, Matrix Biology, 2000, pp. 169-173, vol. 19.

Ryan et al, Differential Expression of a Cysteine-rich Domain in the Amino-terminal Propeptide of Type II (Cartilage) Procollagen by Alternative Splicing of mRNA, J. Biol. Chem., 1990, pp. 10334-10339, vol. 265, No. 18.

Sandell et al, Alternative Splice Form of Type II Procollagen mRNA (IIA) Is Predominant in Skeletal Precursors and Non-Cartilaginous Tissues During Early Mouse Development, Develop. Dyn., 1994, pp. 129-140, vol. 199.

Seo et al, TIMP-2 Mediated Inhibition of Angiogenesis: An MMP-Independent Mechanism, Cell, 2003, pp. 171-180, vol. 114.

Stupack et al, Apoptosis of adherent cells by recruitment of caspase-8 to unligated integrins, J. Cell Biol., 2001, pp. 459-470, vol. 155, No. 3.

Teitelbaum, Osteoclasts, integrins, and osteoporosis, J. Bone Miner. Metab., 2000, pp. 344-349, vol. 18.

Thorogood et al, Transient Expression of Collagen Type II at Epitheliomesenchymal Interfaces during Morphogenesis of the Cartilaginous Neurocranium, Develop. Biol., 1986, pp. 497-509, vol. 116.

Wang et al, Regulation of Adenovirus Membrane Penetration by the Cytoplasmic Tail of Integrin $\beta 5$, J. Virology, 2000, pp. 2731-2739, vol. 74, No. 6.

Wang et al, Annexin V/$\beta 5$ Integrin Interactions Regulate Apoptosis of Growth Plate Chondrocytes, J. Biol. Chem., 2006, pp. 30848-30856, vol. 281, No. 41.

Wu et al, Inhibition of corneal angiogenesis by local application of vasostatin, Molecular Vision, 2005, pp. 28-35, vol. 11.

Ye et al, Design, Synthesis, and Evaluation of Near Infrared Fluorescent Multimeric RGD Peptides for Targeting Tumors, J. Medicinal Chemistry, 2006, pp. 2268-2275, vol. 49, No. 7.

Zhu et al, Type IIA Procollagen Containing the Cysteine-rich Amino Propeptide Is Deposited in the Extracellular Matrix of Prechondrogenic Tissue and Binds to TGF-$\beta 1$ and BMP-2, J. Cell Biol., 1999, pp. 1069-1080, vol. 144, No. 5.

Non-Final Office action dated Apr. 30, 2009 from related U.S. Appl. No. 12/098,942, 25 pages.

Final Office action dated Nov. 27, 2009 from related U.S. Appl. No. 12/098,942, 18 pages.

Zips, New Anticancer Agents: In Vitro and In Vivo Evaluation, In Vivo, 2005, pp. 1-7, vol. 19.

Christiansen, Biological impediments to monoclonal antibody-based cancer immunotherapy, Mol Cancer Ther, 2004, pp. 1493-1501, vol. 3.

Topp, Antibody transport in cultured tumor cell layers, Journal of Controlled Release, 1998, pp. 15-23, vol. 53.

Bowie, Deciphering the Message in Protein Sequences: Tolerance to Amino Acid Substitutions, 1990, pp. 1306-1310, vol. 247.

Tandon, AlphaV Beta 3 Integrin: A Novel Therapeutic Target in Rheumatoid Arthritis, JK Science, Apr.-Jun. 2005, pp. 61-62, vol. 7.

Wilder, Integrin alpha V beta 3 as a target for treatment of rheumatoid arthritis and related rheumatic disease, Ann Rheum Dis, 2002, pp. ii96-ii99, vol. 61 (Suppl II).

Knapp, Antitumor effects of piroxicam in spontaneous canine invasive urinary bladder cancer, a relevant model of human invasive bladder cancer, Eicosanoids and Other Bioactive Lipids in Cancer, Inflammation, and Radiation Injuiry, 2002, pp. 377-380, Kluwer Academic/Plenum Publishers.

Notice of Allowance dated Jan. 6, 2012 from related U.S. Appl. No. 12/836,832, 5 pages.

Non-Final Office action dated Apr. 25, 2011 from related U.S. Appl. No. 12/836,832, 8 pages.

* cited by examiner

|          | exon 5 |  | exon 6 |  | exon 7 |
|----------|--------|--------|--------|--------|--------|
| human    | GPKGPPG | PQGPAGEQG | PGPRGD | KGEKGA | PGPRGRDGEP |
| dog      | GPKGPPG | PQGPAGEQG | PGPRGD | KGEKGA | PGPRGRDGEP |
| horse    | GPKGPPG | PQGPAGEQG | PGPRGD | KGEKGA | PGPRGRDGEP |
| rat      | GPKGPPG | PQGPAGEQG | PGPRGD | KGEKGA | PGPRGRDGEP |
| chicken  | GPRGPPG | PQGPAGEQG | PGPRGD | KGERGA | PGPRGRDGEP |
| xenopus  | GPRGPPG | PQGPSGEQG | SRGERGD | KGEKGA | PGPRGRDGEP |
| zebrfish | GPRGPAGPMG | PPGEQGTRGERGA | KGEKGS | PGPRGRDGEP |

FIG. 2B

A GST

B PIIBNP

INHIBITION OF MIGRATION AND INDUCTION OF CELL DEATH BY THE TYPE II COLLAGEN AMINO PROPEPTIDES

CROSS REFERENCE TO RELATED APPLICATIONS

This application is a divisional of U.S. application Ser. No. 12/836,832 filed Jul. 15, 2010, which is a divisional of U.S. application Ser. No. 12/098,942 filed Apr. 7, 2008, now U.S. Pat. No. 7,851,436, which claims the priority of Provisional Application No. 60/910,361, filed Apr. 5, 2007, all of which are hereby incorporated by reference in their entirety.

GOVERNMENTAL RIGHTS

This invention was made with government support under grant no. R0136994-21 awarded by the National Institute of Arthritis and Musculoskeletal and Skin Diseases. The government has certain rights in the invention.

FIELD OF THE INVENTION

The invention encompasses combinations and methods for inducing cell death, inhibiting angiogenesis, and inhibiting cell migration.

BACKGROUND OF THE INVENTION

Fibrillar collagens are biosynthesized as procollagens with both amino- and carboxy-terminal globular extension peptides. Type II procollagen has two alternative splice forms of the amino-propeptide that either contains a cysteine-rich domain (von Willebrand C) encoded by exon 2 (type IIA) or does not contain exon 2 (type IIB). Type IIA procollagen is present in embryonic basement membranes, developing heart, spine and chondroprogenitor cells while type IIB procollagen is synthesized almost exclusively by chondrocytes (Sandell et al., 1993). The mRNA splice switch from type IIA to IIB procollagen is a sign of commitment to chondrogenesis, or cartilage formation.

Cartilage is avascular and resistant to tumor invasion. A better understanding of the mechanisms that keep cartilage avascular and resistant to tumor invasion may help develop compositions and methods for inducing cell death and inhibiting angiogenesis. Due to the prevalence of tumor related and angiogenesis related disorders, there is a need in the art for methods for inducing cell death and inhibiting angiogenesis.

SUMMARY OF THE INVENTION

One aspect of the present invention encompasses a method for inducing cell death in a cell that expresses an $\alpha_v\beta_3$ and/or an $\alpha_v\beta_5$ integrin. The method comprises contacting the cell with an isolated Type IIB collagen amino propeptide.

Another aspect encompasses a method for inhibiting angiogenesis in a subject. The method comprises contacting a cell that expresses an $\alpha v\beta 3$ and/or an $\alpha v\beta 5$ integrin with a Type IIB collagen amino propeptide.

Yet another aspect of the invention encompasses a method for inducing the death of a tumor cell expressing an $\alpha v\beta 3$ and/or an $\alpha v\beta 5$ integrin. The method comprises administering to the cell a Type IIB collagen amino propeptide.

Still another aspect of the invention encompasses a combination. The combination comprises a Type IIB collagen amino propeptide and an agent selected from the group consisting of an imaging agent and a therapeutic agent.

Other aspects and iterations of the invention are described more thoroughly below.

REFERENCE TO COLOR FIGURES

The application file contains at least one photograph executed in color. Copies of this patent application publication with color photographs will be provided by the Office upon request and payment of the necessary fee.

BRIEF DESCRIPTION OF THE FIGURES

FIG. 9A shows representative corneas after implantation of FGF pellets and treatment with PIIBNP or mPIIBNP. The inhibition of angiogenesis by PIIBNP was notable from the suppression of neovascularization in mouse corneas. FIG. 9B shows a quantitation of neovascularization in mouse corneas transplanted with FGF pellets and treated with PIIBNP or mPIIBNP. The total vessel outgrowth was measured based on the fluorescently stained blood vessels using Metamorph software.

DETAILED DESCRIPTION OF THE INVENTION

Figure 1:
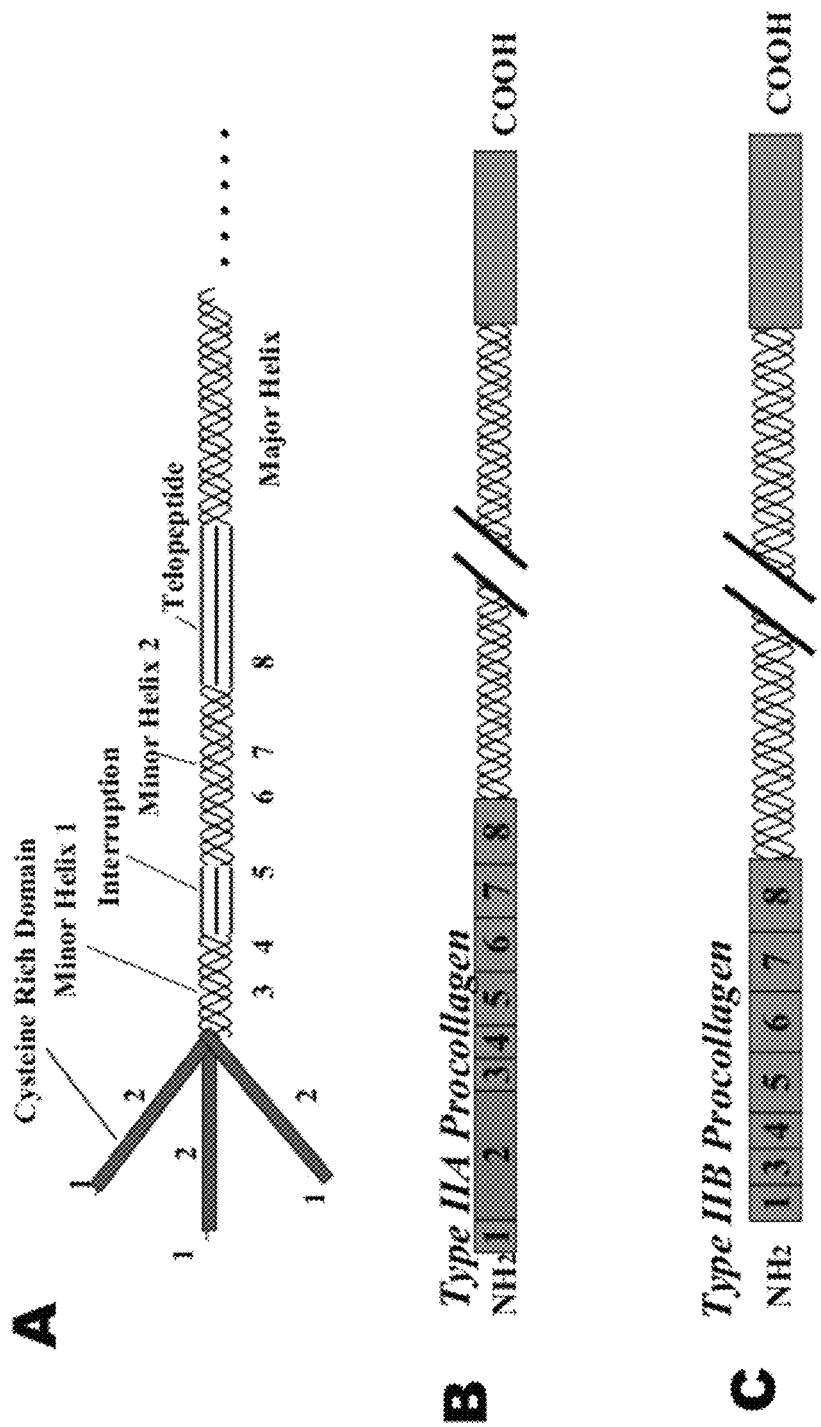
FIG. 1 depicts illustrations of the gene and protein structures of collagen Type II $NH_2$-propeptides. The Type IIA $NH_2$-propeptide (PIIANP) portion of the gene is comprised of the eight exons that are represented by numbers (FIGS. 1A and B). The solid red area indicates the cysteine-rich domain encoded by exon 2; wavy lines are Gly-X-Y sequence; and straight lines are non-Gly-X-Y. In comparison, Type IIB (PIIBNP) is comprised of 7 exons, excluding the cystein-rich exon 2 (FIG. 1C).

It has been discovered, as detailed in the examples, that a splice variant of the Type II procollagen amino propeptide can induce cell death, inhibit angiogenesis, and/or inhibit cell migration. The present invention, accordingly, includes compositions and methods for inducing cell death, inhibiting angiogenesis, or inhibiting cell migration of a cell or a population of cells. Further, the present invention may be beneficial for the treatment of tumor cell migration and metastasis, detrimental angiogenesis (for example as seen in wet macular degeneration), tumor formation and growth, osteoporosis, cartilage repair and other diseases where targeted cell death and inhibiting angiogenesis or migration may be advantageous.

I. Compositions of the Invention

A composition of the invention typically comprises at least one splice variant of Type II collagen amino propeptide. The Type II collagen amino propeptide has two known splice variants, Type IIA and Type IIB. Additionally, the invention encompasses a combination of a Type II collagen amino propeptide and at least one agent. Suitable agents may include, but are not limited to, imaging agents, treatment agents, or a combination thereof. The invention also provides pharmaceutical compositions comprising a propeptide, as detailed below.

(a) Type II Collagen Amino Propeptides

Type II procollagen is synthesized in two mRNA splice forms that differ by the inclusion (Type IIA) or exclusion (Type IIB) of exon 2. Both of the Type II procollagen amino propeptides contain two adjacent RGD amino acid motifs, encoded in exon 6, and both propeptides bind to cells via the integrins $\alpha_V\beta_3$ or $\alpha_V\beta_5$. The present invention contemplates Type II collagen amino propeptides and variants or fragments thereof. In one embodiment, the invention includes the full-length Type IIA amino propeptide, as well as variants or fragments thereof. In another embodiment, the invention includes the full-length Type IIB amino propeptide, as well as variants or fragments thereof. The sequences of the Type IIA and Type IIB amino propeptides are known in the art. Generally speaking, a propeptide sequence may be derived from a human, a mouse, or any other animal that expresses a Type II collagen amino propeptide, such as those detailed in FIG. 2B. In an exemplary embodiment, the propeptide is human.

The invention also encompasses variants of type II collagen amino propeptides that may be mutated, or altered, to enhance, or change, biological properties of the protein. Such biological properties may include in vivo and/or in vitro stability (e.g., half-life), localization, and folding properties. Suitable mutations may include single amino acid changes, deletions of one or more amino acids, N-terminal truncations, C-terminal truncations, insertions, etc. Additionally, variants may include fusions of a propeptide to another agent, protein, or biomolecule. Variants may be generated using standard techniques of molecular biology, including random mutagenesis and targeted mutagenesis as described in the Examples herein and Current Protocols in Molecular Biology, Unit 8, pub, John Wiley & Sons, Inc., 2000, incorporated herein by reference.

In certain aspects, a variant may be a homolog, ortholog, mimic or degenerative variant of a propeptide is also suitable for use in the present invention. A number of methods may be employed to determine whether a particular homolog, mimic or degenerative variant possesses substantially similar biological activity relative to a propeptide. For instance, activity may be determined using assays described in the Examples.

In addition to having a substantially similar biological function, a homolog, ortholog, mimic or degenerative variant suitable for use in the invention will also typically share substantial sequence similarity to a propeptide. For example, suitable homologs, ortholog, mimic or degenerative variants preferably share at least 30% sequence homology, more preferably, 50%, and even more preferably, are greater than about 75% homologous in sequence to a propeptide of the invention. Alternatively, peptide mimics may be used that retain critical molecular recognition elements, although peptide bonds, side chain structures, chiral centers and other features of the parental active protein sequence may be replaced by chemical entities that are not native to a propeptide yet, nevertheless, confer activity.

In determining whether a polypeptide is substantially homologous to a propeptide, sequence similarity may be determined by conventional algorithms, which typically allow introduction of a small number of gaps in order to achieve the best fit. In particular, "percent homology" of two polypeptides or two nucleic acid sequences is determined using the algorithm of Karlin and Altschul [(Proc. Natl. Acad. Sci. USA 87, 2264 (1993)]. Such an algorithm is incorporated into the NBLAST and XBLAST programs of Altschul, et al. (J. Mol. Biol. 215, 403 (1990)). BLAST nucleotide searches may be performed with the NBLAST program to obtain nucleotide sequences homologous to a nucleic acid molecule of the invention. Equally, BLAST protein searches may be performed with the XBLAST program to obtain amino acid sequences that are homologous to a polypeptide of the invention. To obtain gapped alignments for comparison purposes, Gapped BLAST is utilized as described in Altschul, et al. (Nucleic Acids Res. 25, 3389 (1997)). When utilizing BLAST and Gapped BLAST programs, the default parameters of the respective programs (e.g., XBLAST and NBLAST) are employed. See www.ncbi.nlm.nih.gov for more details.

Additionally, the invention encompasses biologically active fragments of propeptides and/or fragments corresponding to functional domains of a propeptide. Fragments of interest may typically be at least about 10 amino acids (aa) in length, usually at least about 50 aa in length, more preferably 60, 70, 80, 90, 100, 105, 110, 120, 130, 140, or 150 aa in length and may be as long as 160, 170, 174, 175, 180, 190, 200, 220, 240, 260, 280 or 300 aa in length or even longer. A fragment may typically have a stretch of amino acids that is identical to a propeptide of at least about 10 aa, and usually at least about 15 aa, and in many embodiments at least about 50, 60, 70, 80, 90, 100, 110, 120, 130, 140, or 150 aa in length. A skilled artisan will recognize that a protein fragment can retain all or substantially all of a biological property of the isolated protein.

Propeptides suitable for use in the invention are typically isolated or pure and are generally administered as a composition in conjunction with a suitable pharmaceutical carrier, as detailed below. A pure polypeptide constitutes at least about 90%, preferably, 95% and even more preferably, at least about 99% by weight of the total polypeptide in a given sample.

The peptides or proteins of the invention may be generated synthetically or by recombinant techniques, and may be purified according to known methods, such as precipitation (e.g. ammonium sulfate), HPLC, ion exchange chromatography, affinity chromatography (including immunoaffinity chromatography) or various size separations (sedimentation, gel electrophoresis, gel filtration). As an example, a Type II collagen propeptide may be produced by cultivating a host cell expressing a Type II collagen propeptide and then isolating the protein. Such methods include the introduction of an expression vector containing at least one propeptide of the invention into a host cell, cultivation of the subject protein containing host cell, and isolation of the subject protein from the cell extract. Methods to cultivate host cells are known in the art. Methods to express and isolate a propeptide are described in the Examples herein and in additional details may be found in Current Protocols in Protein Science, Units 5, pub. John Wiley & Sons, Inc., 2002 and Current Protocols in Protein Science, Units 6, pub. John Wiley & Sons, Inc., 2002, both hereby incorporated by reference in their entirety.

(b) Nucleic Acids

The invention also encompasses nucleic acid sequences that encode Type II collagen propeptides or a variant or fragment thereof. The nucleic acid may encode a peptide or polypeptide containing all or part of the Type II collagen amino propeptide amino acid sequence. Nucleic acid sequences of the invention may also arise as a consequence of codon redundancy and functional equivalency that are known to occur naturally within nucleic acid sequences. Alternatively, functionally equivalent proteins or peptides may be created by the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the stability of the protein.

The nucleic acid sequences used in the present invention, regardless of the length of the coding sequence itself, may be combined with other nucleic acid sequences, such as promoters, enhancers, polyadenylation signals, origin of replication, and selectable markers, as well as other coding sequences, such that their overall length may vary considerably.

It is contemplated that a nucleic acid of the present invention may encode a full-length propeptide or encode a truncated version of the propeptide, for example a truncated Type IIB collagen amino-propeptide polypeptide. Alternatively, a nucleic acid sequence may encode a full-length polypeptide sequence with additional heterologous coding sequences, for example to allow for purification of the polypeptide, transport, secretion, post-translational modification, or for therapeutic benefits such as targeting or efficacy.

Methods for using a nucleic acid of the invention to produce a propeptide of the invention are known in the art. For instance, methods for introducing a DNA sequence into eukaryotic cells are known in the art and typically include the use of a DNA vector or plasmid. There are many vectors known and available in the art. One of skill in the art will recognize that the selection of a particular vector depends upon the intended use of the nucleic acid. Preferably, the DNA sequences are introduced by a vector, or plasmid, capable of transforming and driving the expression of the components of the nucleic acid in the desired cell type, whether that cell type is prokaryotic or eukaryotic. Many vectors comprise sequences allowing both prokaryotic vector replication and eukaryotic expression of operably linked nucleic acid sequences.

Vectors useful according to the invention may be autonomously replicating, that is, the vector exists extrachromosomally, and its replication is not necessarily directly linked to the replication of the host genome. Alternatively, the replication of the vector may be linked to the replication of the host chromosomal DNA. For example, the vector may be integrated into a chromosome of the host cell as achieved by retroviral vectors.

A vector will typically comprise sequences operably linked to a nucleic acid of the invention that permits the transcription and translation of the components when appropriate. Within the expression vector, a nucleic acid of the invention may be linked to a regulatory sequence as appropriate to obtain the desired expression properties. These regulatory sequences may include promoters (attached either at the 5' end of the sense strand or at the 3' end of the antisense strand), enhancers, terminators, operators, repressors, and inducers. The promoters may be regulated or constitutive. In some situations it may be desirable to use conditionally active promoters, such as tissue-specific or developmental stage-specific promoters. The expression vector may provide a transcriptional and translational initiation region, which may be inducible or constitutive, where the coding region is operably linked under the transcriptional control of the transcriptional initiation region, and a transcriptional and translational termination region. These control regions may be native to the subject species from which nucleic acid is obtained, or may be derived from exogenous sources.

Expression vectors generally have convenient restriction sites located near the promoter sequence to provide for the insertion of nucleic acid sequences encoding heterologous proteins. Additionally, a selectable marker operative in the expression host may be present. Expression vectors may be used for, among other things, the production of fusion proteins.

A skilled artisan will recognize that the choice of vector for use with the invention is dependent on the host with which the invention will be utilized. Suitable vectors include, but are not limited to, plasmids, cosmids, artificial chromosomes, bacteriophage-derived vectors, viral vectors, retroviral vectors, adenoviral vectors, adeno-associated viral vectors, herpesviral vectors, insect vector systems and synthetic vectors. One of skill in the art would be well equipped to construct any number of vectors through standard recombinant techniques as described in Maniatis et al., 1990 and Ausubel et al., 1994, both incorporated herein by reference.

Non-viral vectors, such as plasmids and cosmids, require suitable methods for delivery into cells. Such methods commonly known in the art include, but are not limited to direct delivery of DNA by: injection microinjection, electroporation, calcium phosphate precipitation, using DEAE-dextran followed by polyethylene glycol, direct sonic loading, liposome-mediated transfection, receptor-mediated transfection, microprojectile bombardment, agitation with silicon carbide fibers, desiccation/inhibition-mediated DNA uptake, and any combination of such methods. Through the application of techniques such as these, organelle(s), cell(s), tissue(s) or organism(s) may be stably or transiently transformed. In certain embodiments, acceleration methods are preferred and include, for example, microprojectile bombardment or inhalation methods.

(c) Combinations

A combination of the invention typically comprises a propeptide, as described above, and at least one agent selected from an imaging agent and a treatment agent. In one embodiment, the combination may comprise an imaging agent. In an alternative embodiment, the combination may comprise a treatment agent. In still another alternative embodiment, the combination may comprise an imaging agent and a treatment agent. Irrespective of the embodiment, the agent(s) may be conjugated to the propeptide by a covalent bond or conjugated via a linker. Alternatively, the agent(s) may be combined with a propeptide of the invention to form a composition. In yet another alternative, a combination of the invention may comprise a composition comprising a propeptide, and a composition comprising at least one agent.

i. Imaging Agents

Several imaging agents are suitable for use to the extent that they provide the ability to detect or monitor the localization of a propeptide of the present invention. In one embodiment, the imaging agent comprises an optical imaging agent. Optical imaging agents suitable for use in the invention can and will vary depending on the embodiment, but may include fluorophores, organic fluorescent dyes, luminescent imaging agents, fluorescent lanthanide complexes, and fluorescent semiconductor nanocrystals. Examples of suitable visible (400-700 nm) fluorescent dyes include fluorescein, FITC, rhodamine, Texas Red, CyDyes (e.g., Cy3, Cy5, Cy5.5), Alexa Fluors (e.g., Alexa$^{488}$, Alexa$^{555}$, Alexa$^{594}$; Alexa$^{647}$) and DyDelight Dyes. Examples of suitable near infrared (NIR) (700-900 nm) fluorescent dyes include carbocyanine dyes, such as cypate and its derivatives. Luminescence imaging agents include luminescent lanthanide chelates and bioluminescence compounds (e.g., bacterial Lux, eukaryotic Luc or Ruc systems).

In an alternative embodiment, the imaging agent is a radiological imaging agent. A variety of radioisotopes that are capable of being detected, such as in a PET or SPECT diagnostic imaging procedure, are suitable for use in the present invention. Suitable examples of radiological imaging agents may include Antimony-124, Antimony-125, Arsenic-74, Barium-103, Barium-140, Beryllium-7, Bismuth-206, Bismuth-207, Cadmium-109, Cadium-115, Calcium-45, Cerium-139, Cerium-141, Cerium-144, Cesium-137, Chromium-51, Gadolinium-153, Gold-195, Gold-199, Hafnium-175-181, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185, Palladium-103, Platinum-195, Praseodymium-143, Promethium-147, Protactinium-233, Radium-226, Rhenium-186, Rubidium-86, Ruthenium-103, Ruthenium-106, Scandium-44, Scandium-46, Selenium-75, Silver-110, Silver-111, Sodium-22, Strontium-85, Strontium-89, Strontium-90, Sulfur-35, Tantalum-182, Technetium-99, Tellurium-125, Tellurium-132, Thallium-204, Thorium-228, Thorium-232, Thallium-170, Tin-113, Titanium-44, Tungsten-185, Vanadium-48, Vanadium-49, Ytterbium-169, Yttrium-88, Yttrium-90, Yttrium-91, Zinc-65, and Zirconium. In a further alternative embodiment, the radiological imaging agent may be selected from the group consisting of Technecium-99, Indium-111, Strontium-90, Iodine-125, Thallium-201, fluorine-18, carbon-11, carbon-13, nitrogen-13, Oxygen-15, Copper-64, Lutetium-177, Yttrium-90, and Iodine-131

A variety of other imaging agents may be suitable for use in the invention. For example, other imaging agents may include, gadolinium, metalloporphyrins, ferric chloride, ferric ammonium citrate, and ferrioxamine methanesulfonate for magnetic resonance imaging.

ii. Treatment Agents

In the context of the present invention, it is contemplated that Type IIB or Type IIA collagen amino propeptides, or variants thereof may be used alone or in combination with an additional treatment agent as a more effective therapy.

Additional treatment agents contemplated for use in combination with Type IIB or Type IIA collagen amino propeptides or variants thereof include traditional anticancer therapies. Anticancer agents may include but are not limited to, chemotherapy, radiotherapy, hormonal therapy or immunotherapy that targets cancer/tumor cells.

Non-limiting examples of chemotherapeutic agents may include any drug or agent known in the art to have utility for treating or preventing neoplasia disorders or related diseases. In one embodiment, the antineoplastic agent is an antimetabolite including folate antagonists (e.g. methotrexate), pyrimidine antagonists (e.g. cytarabine, floxuridine, fludarabine, fluorouracil, and gemcitabine), purine antagonists (e.g. cladribine, mercaptopurine, thioguanine), and adenosine deaminase inhibitors (e.g. pentostatin). In an alternative embodiment, the antineoplastic agent is an alkylating agent such as chlorambucil, cyclophosphamide, busulfan, ifosfamide, melphalan, and thiotepa. In yet another embodiment, the antineoplastic agent is an alkylator agent such as cisplatin, carboplatin, procarbazine, dacarbazine, and altretamine. In still another embodiment, the antineoplastic agent is an antitumor antibiotic such as bleomycin, dactinomycin, and mitomycin. In yet a further embodiment, the antineoplastic agent is an immunological agent such as interferon. In another embodiment, the antineoplastic agent is a plant alkaloid including vinca alkaloids (e.g. vinblastine, vincristine and vinorelbine), epipodophyllotoxins (e.g. etoposide and teniposide), taxanes (e.g. docetaxel and paclitaxel), and camptothecins (e.g. topotecan and irinotecan). Of course those skilled in the art will appreciate that the particular antineoplastic agents to be administered with the compound(s) of the invention will vary considerably depending on the type of neoplasia disorder being treated and its stage of progression, and may include any analog or derivative variant of the foregoing. One skilled in the art will recognize that dosages of the above compounds can and will vary depending upon the subject and the type of neoplasia.

Radiotherapeutic agents may also be used in combination with the Type IIB or Type IIA collagen amino propeptides, proteins or derivatives of the present invention. Non-limiting examples may include factors that cause DNA damage, such as γ-rays, X-rays, and/or the directed delivery of radioisotopes to tumor cells. Other forms of DNA damaging factors are also contemplated such as microwaves and UV-irradiation. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the target cell.

Immunotherapeutics may also be employed in the present invention in combination with Type IIB or Type IIA collagen amino propetides, or variant or a fragment thereof. Immunotherapeutics generally rely on the use of immune effector cells and molecules to target and destroy cancer cells. The immune effector may be, for example, an antibody specific for a marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Hormonal therapy may also be used in conjunction with a Type IIB or Type IIA collagen amino propeptides or variant thereof, or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

It is further contemplated that other agents may be used in combination with the present invention to improve the therapeutic efficacy of treatment. These additional agents may include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increased intercellular signaling by elevating the number of GAP junctions would increase the anti-hyperproliferative effects on the neighboring hyperproliferative cell population. In other embodiments, cytostatic or differentiation agents may be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

(d) Pharmaceutical Compositions

The present invention encompasses pharmaceutical compositions comprising a propeptide of the invention. In some embodiments, the present invention encompasses a pharmaceutical composition comprising a combination of the invention. Pharmaceutical forms suitable for use in the invention may include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. Composition(s) of absorption delay agents (aluminum monostearate and gelatin) may also be used. It must be stable under the conditions of manufacture and storage and must be preserved against the contaminating action of microorganisms, such as bacteria and fungi. The carrier may be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

For parenteral administration in an aqueous solution, for example, the solution should be suitably buffered if necessary and the liquid diluent first rendered isotonic with sufficient saline or glucose (see for example, "Remington's Pharmaceutical Sciences" 15th Edition, pages 1035-1038 and 1570-1580). These particular aqueous solutions are especially suitable for subcutaneous, intramuscular, and intratumoral administration. In this connection, sterile aqueous media that may be employed will be known to those of skill in the art in light of the present disclosure. Variation in dosage will necessarily occur depending on the condition of the subject being treated; the severity of the condition; and will be determined by the person administering the dose. For human administration, preparations should meet sterility, pyrogenicity, general safety and purity standards as required by FDA Office of Biologics standards.

The compositions of the present invention may be formulated in a neutral or salt form. Pharmaceutically-acceptable salts may include the acid addition salts (formed with the free amino groups of the protein) which are formed with inorganic acids; or salts (formed with the free carboxyl groups) derived from inorganic bases as is known to those of ordinary skill in the art.

A pharmaceutical composition may also comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the treatment compositions is contemplated. Supplementary active ingredients may also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art.

In general, the dosage of compositions comprising a Type IIA or Type IIB collagen amino propeptide will vary depending upon such factors as the recipient's age, weight, height, sex, general medical condition and previous medical history. For example, it is typically desirable to provide the recipient with a dosage of composition comprising a Type IIA or Type IIB collagen amino propeptide in the range of from about 1 pg/kg to 10 mg/kg (amount of agent/body weight of patient), although a lower or higher dosage also may be administered as circumstances dictate. It is preferred that the amount of Type IIA or Type IIB collagen amino propeptide contacted with a cell ranges from about 600 nM to about 3.0 µM. Range finding studies may be conducted to determine appropriate dosage by techniques known to those skilled in the art and as described in *Current Protocols in Pharmacology*, Unit 10, pub. John Wiley & Sons, 2003, hereby incorporated by reference in its entirety. A skilled artisan will recognize the effective amount for each active compound may vary with factors including, but not limited to, the activity of the compound used, stability of the active compound in the recipient's body, the total weight of the recipient treated, the route of administration, the ease of absorption, distribution, and excretion of the active compound by the recipient, the age and sensitivity of the recipient to be treated, the type of tissue, and the like.

Treatment of a disorder or disease, such as those listed herein, would generally include contacting a cell with a Type IIB or Type IIA collagen amino propeptide or an expression construct encoding a Type IIB or Type IIA collagen amino propeptide. One exemplary method for the delivery of a peptide or an expression construct is via injection. Another exemplary method for delivery is via a biological matrix, gel, or scaffold. Administration may also be parenteral, intradermal, intramuscular, or intratumioral administration. Other administration routes include lavage, continuous perfusion, topical and oral administration and formulation.

II. Methods of the Invention

Another aspect of the present invention includes methods for inducing cell death, inhibiting angiogenesis, and inhibiting cell migration. Generally speaking, the RGD sequence of a propeptide of the invention serves as the primary integrin recognition site. It has been discovered that the propeptides of the invention bind to $\alpha_v\beta_3$ and/or $\alpha_v\beta_5$ integrins. These integrins are typically expressed on endothelial cells, cancer cells, and osteoblasts. When a Type IIB propeptide of the invention binds to a cell expressing an $\alpha_v\beta_3$ and/or $\alpha_v\beta_5$ integrin, the propeptide usually induces cell death, inhibits angiogenesis, and/or inhibits cell migration, as described in more detail below.

The methods of the present invention may be used to treat a mammalian subject. Such mammalian subjects may include, but are not limited to, humans, non-human primates, companion animals, laboratory animals, and livestock animals. Non-limiting examples of companion animals may include dogs, cats, horses, rabbits, and the like. Non-limiting examples of livestock animals may include mammals with significant commercial value (e.g., dairy cows, beef cattle, sporting animals). Non-limiting examples of laboratory animals may include mice, rats, guinea pigs, and the like.

(a) Inducing Cell Death

In one embodiment, the invention provides a method for inducing cell death in a cell that expresses an $\alpha_v\beta_3$ and/or an $\alpha_v\beta_5$ integrin. A further aspect of the invention provides a method for inducing cell death in a cell that expresses $\alpha_v\beta_3$ and/or $\alpha_v\beta_5$ integrins, such that the cell death that results is independent of detachment mediated cell death. The method comprises contacting the cell with a Type IIB propeptide of the invention, as detailed above, such that cell death results. Cell death may be measured by the methods described herein (Example 3) and by methods commonly known in the art. In some embodiments, the cell is a tumor cell that expresses an $\alpha_v\beta_3$ and/or $\alpha_v\beta_5$ integrin.

To induce cell death using the methods and compositions of the present invention, one would generally contact a cell with a Type IIB propeptide of the invention. In some embodiments, one would contact a cell with a combination of the invention, as detailed in section I above. A combination may comprise a propeptide and an agent in a combined amount effective to induce cell death. The propeptide and the agent may be administered simultaneously. This may be achieved by contacting the cell with a single composition or pharmacological formulation that includes both a propeptide and an agent, or by contacting the cell with two distinct compositions or formulations, at the same time, wherein one composition includes a Type IIB propeptide and the other includes the additional agent.

Alternatively, administration of a propeptide may precede or follow the administration of an additional agent by intervals ranging from minutes to weeks. In embodiments where the additional agent is administered separately to the cell, one would generally ensure that a significant period of time did not expire between the time of each delivery, such that the agent would still be able to exert an advantageously combined effect on the cell with the propeptide. In such instances, it is contemplated that one would contact the cell with both modalities within about 12-24 hours of each other and, more preferably, within about 6-12 hours of each other, with a delay time of only about 12 hours being exemplary. Thus, therapeutic levels will be maintained. In some situations, it may be desirable to extend the time period for treatment significantly (for example, to reduce toxicity). Thus, several days (2, 3, 4, 5, 6 or 7) to several weeks (1, 2, 3, 4, 5, 6, 7 or 8) may lapse between the respective administrations. It also is conceivable that more than one administration of a propeptide in combination with an additional anticancer agent may be desired.

The methods of the present invention may be used to induce cell death of tumor cells derived from different types of neoplasia or neoplasia related disorders irrespective of the stage of progression. In some aspects, the methods may be used to induce tumor cell death to prevent the onset of a clinically evident neoplasia altogether or to prevent the onset of a preclinical evident stage of a neoplasia in subjects at risk for developing neoplasia. In other aspects, the methods may be used to induce tumor cell death to prevent the initiation, growth, or spreading of benign cells. In still other aspects, the methods may be used to induce tumor cell death to prevent the transformation of premalignant cells to malignant cells or to arrest or reverse the progression of premalignant cells to malignant cells. In further aspects, the methods may be used to induce tumor cell death to inhibit neoplasia growth, spreading or metastasis.

In one embodiment, the neoplasia may be an epithelial cell-derived neoplasia (epithelial carcinoma). By way of example, epithelial cell-derived neoplasia may include basal cell carcinoma, squamous cell carcinoma or adenocarcinoma. In another embodiment, the neoplasia may be a gastrointestinal cancer. Gastrointestinal cancers may include lip cancer, mouth cancer, esophageal cancer, small bowel cancer, stomach cancer and colon cancer. In still another embodiment, the neoplasia may be liver cancer, bladder cancer, pancreas cancer, ovary cancer, cervical cancer, lung cancer, breast cancer and skin cancer, such as squamous cell and basal cell cancers, prostate cancer, brain cancer and renal cell carcinoma. In yet another embodiment, the cells may be adenomatous polyps, including those with familial adenomatous polyposis (FAP). In another embodiment, the cells may be leukemia cells. In still another embodiment, the cells may be derived from tumor metastasis.

Additionally, tumor cells contemplated by the present invention include, but are not limited to, cells from head and neck cancer, bone cancer (including chondrosarcoma), bone marrow cancer, gum cancer, kidney cancer, liver cancer, nasopharynx cancer, testis cancer, tongue cancer, or uterine cancer.

In certain embodiments, the invention provides a method for inducing cell death in osteoclasts. In particular, the invention provides a method for inducing cell death in an osteoclast that expresses an $\alpha_V\beta_3$ and/or $\alpha_V\beta_5$ integrin. The method comprises contacting the osteoclast with a Type IIB propeptide of the invention. Inducing the death of an osteoclast may be used to treat disorders related to bone degradation, such as osteoporosis.

(b) Inhibiting Angiogenesis

In some embodiments, the present invention also provides a method for inhibiting angiogenesis. In particular, the invention provides a method for inhibiting angiogenesis in a cell that expresses an $\alpha_V\beta_3$ and/or $\alpha_V\beta_5$ integrin. The method comprises contacting the cell with a Type IIB propeptide of the invention, such that angiogenesis is substantially inhibited or reduced. As used herein, "substantially inhibited" refers to inhibiting at least 10%, 20%, 30%, 40%, 50%, 60%, 70%, 80%, 90%, or 100% of angiogenesis, compared to an untreated control. Angiogenesis can be measured by the methods described herein (Example 4) and by methods commonly known in the art.

The methods of the present invention may be used to treat conditions that may benefit from the inhibition of angiogenesis. Exemplary pathologies that involve excessive angiogenesis include cancer (both solid and hematologic tumors), cardiovascular diseases (such as atherosclerosis and restenosis), chronic inflammation (rheumatoid arthritis, Crohn's disease), diabetes (diabetic retinopathy), psoriasis, endometriosis, neovascular glaucoma, macular degeneration, and adiposity.

(c) Migration

The invention also provides a method for inhibiting cell migration. In particular, the invention provides a method for inhibiting migration of a cell that expresses an $\alpha_V\beta_3$ and/or $\alpha_V\beta_5$ integrin. The method comprises contacting the cell with a Type IIB propeptide of the invention, such that migration is inhibited or reduced. Migration may be measured by methods commonly known in the art.

DEFINITIONS

An "anti-cancer agent" is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Anti-cancer agents include biological agents (biotherapy), chemotherapy agents, hormonal therapy agents, gene therapy agents, and radiotherapy agents.

A "tumor cell" as referred to herein, refers to a cell that exhibits unregulated proliferation and gives rise to daughter cells that also exhibit unregulated proliferation. A "tumor cell" can reside in vitro, in vivo, or ex vivo and may be part of a population, part of a tumor, part of a tissue, or part of a subject. Further, as used herein, the term "tumor" and or "cancer" refers to a "tumor cell" and any named neoplasia refers to a "tumor cell". For example, "breast cancer" refers to a type of "tumor cell".

A "cell" as referred to herein, encompasses a single cell, more than one cell, and a population of cells. The cell may be part of a population, part of a tissue, or part of a subject. Further, the cell may reside in vitro, in vivo, or ex vivo.

The term "cell death" refers to programmed or non-programmed cell death and includes apoptosis, autophagic cell death, necrosis, and other non-apoptotic programmed cell death pathways. Essentially, "cell death" refers to the death of a cell regardless of the means associated with that death.

The terms "contact", "contacting", "administer" and "administering" refer to the delivery of a propeptide or combination of the invention to a cell. The terms include administration methods known in the art such as delivery by recombinant DNA, expression vector, transfection, transformation, exogenous application, injection, microinjection, particle bombardment, and others known in the art.

As used herein the term "effective amount" is defined as an amount of the agent (such as the polypeptide or a combination of the polypeptide and an other agent) that is sufficient to detectably ameliorate, reduce, minimize or limit the extent of the disease or biological process. In certain highly preferred embodiments, it also includes elimination, eradication or cure of disease.

As used herein the term "isolated" is meant to describe a polynucleotide, a nucleic acid, a protein, a polypeptide, an antibody, or a host cell that is in an environment different from that in which the polynucleotide, nucleic acid, protein, polypeptide, antibody, or host cell naturally occurs. In reference to a sequence, such as nucleic acid or amino acid, "isolated" includes sequences that are assembled, synthesized, amplified, or otherwise engineered by methods known in the art.

The term "operably linked" or "operatively linked" refers to the association of nucleic acid sequences on a single nucleic acid fragment so that the function of one is regulated by the other or is not hindered by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. Generally, operably linked means that the nucleic acid sequences being linked are contiguous and, where necessary to join two protein coding regions, contiguous and in the same reading frame.

The term "treat" or "treatment" includes partial or total inhibition of the neoplasia growth, spreading or metastasis, as well as partial or total destruction of the neoplasia cells. Treatment also includes prevention of a neoplasia or related disorder. The term treat also includes partial or total inhibition of inflammation or an inflammation related disorder. Treatment also includes prevention of an inflammation or inflammation related disorder.

As various changes could be made in the above compositions and methods without departing from the scope of the invention, it is intended that all matter contained in the above description and in the examples given below, shall be interpreted as illustrative and not in a limiting sense.

EXAMPLES

The following examples illustrate various embodiments of the invention.

Example 1

Type II Procollagen

Fibrillar collagens, types I, II, III, V and XI are biosynthesized as procollagens containing $NH_2$- and COOH-terminal extension peptides. Type II procollagen amino propeptide (FIG. 1A) has two alternative splice forms of the $NH_2$-propeptide that either contains a cysteine-rich von Willebrand C domain, encoded by exon 2 (Type IIA) (FIG. 1B), or does not contain exon 2 (Type IIB) (FIG. 1C). Generally, the $NH_2$- and COOH-terminal peptides of fibrillar collagens are removed prior to deposition of the collagen monomers into fibrils in the extracellular matrix. Type IIA procollagen is present in embryonic basement membranes, heart, spine, eye, and chondroprogenitor cells while Type IIB procollagen is synthesized almost exclusively by chondrocytes. Indeed, the mRNA splice switch from Type IIA to IIB procollagen is a sign of commitment to chondrogenesis.

Figure 2A:
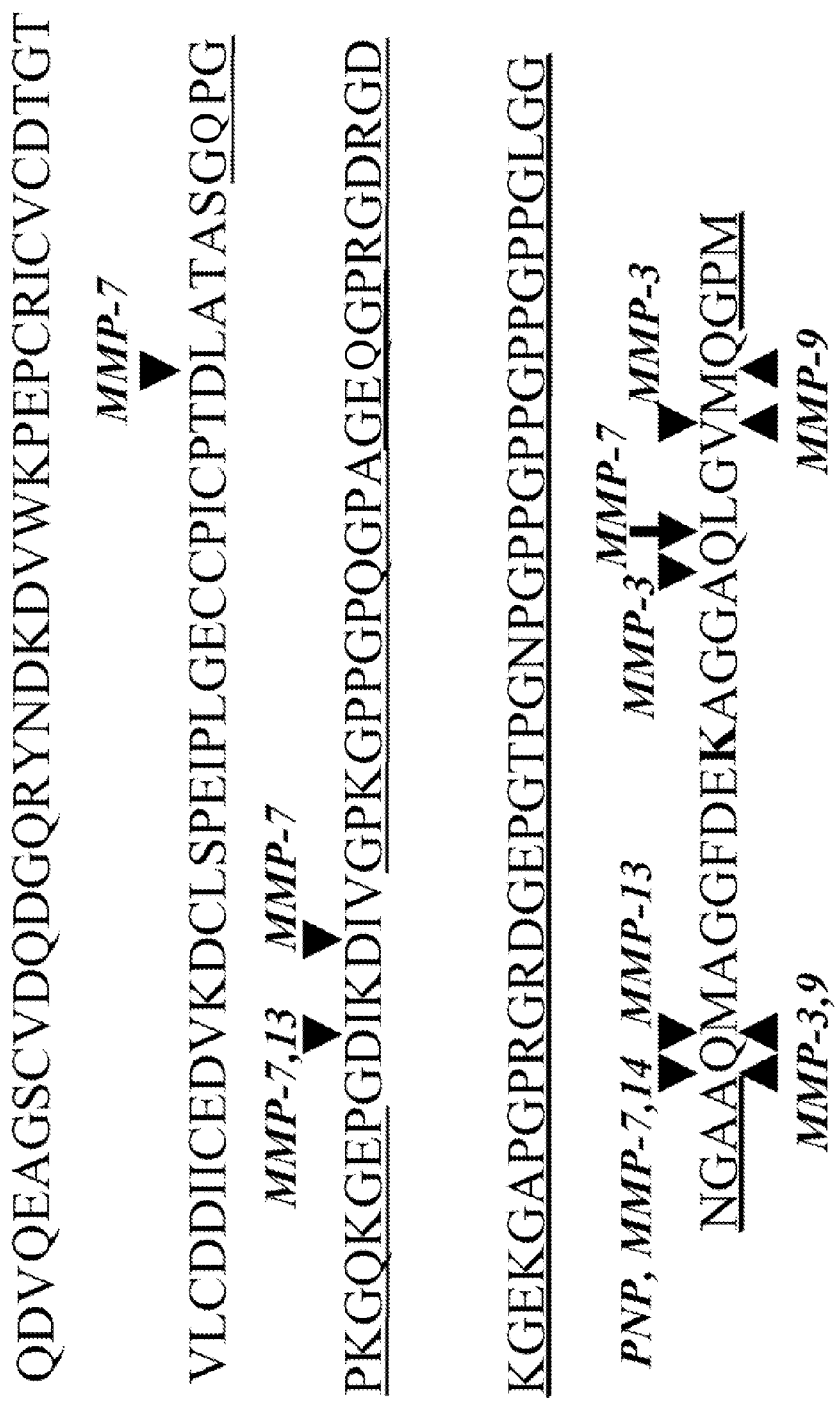
FIG. 2 depicts type II collagen amino-propeptide amino acid sequence information. The amino acid sequence encoding Type II collagen amino-propeptide includes sequence specific to Type II collagen (yellow); the Type IIA specific exon 2 (pink); and multiple matrix metalloproteinase (MMP) cleavage sites (FIG. 2A).
FIG. 2B shows the conservation of the RGD motif across species. The conserved RGDRGD motifs in Type II collagen $NH_2$-propeptides from different species are boxed.

Type II procollagen is unique among the fibrillar collagens in containing vicinal RGD motif in the $NH_2$-terminal propeptide domain (FIG. 2A), a pattern well conserved through various species (FIG. 2B). RGD peptides serve as the primary integrin recognition sites in extracellular matrix proteins and, as such, play an important role in regulating cell/matrix interactions required for proper cell function. The function of RGD-encoded regions in Type II procollagen $NH_2$-propeptide apparently are unique to cartilage. As detailed in the following examples, the Type IIB propeptide is able to induce and maintain important biological properties including angiogenesis, migration, and cell death.

Example 2

PIIBNP Binds to Cells Via Integrins $\alpha_v\beta_3$ and $\alpha_v\beta_5$

Integrins are cell surface receptors that are composed of two subunits, $\alpha$ and $\beta$. Each $\alpha\beta$ combination has its own binding specificity and signaling properties. Generally, integrins are involved in cell-matrix and cell-cell interactions. The $\alpha_v\beta_3$ and $\alpha_v\beta_5$ integrins are closely related and are upregulated during disease processes. Both $\alpha_v\beta_3$ and $\alpha_v\beta_5$ integrins bind to a repertoire of RGD-containing ligands including vitronectin, fibronectin, von Willebrand Factor, proteolysed fragments of collagen, Laminin, and osteopontin. Cells that primarily express $\alpha_v\beta_3$ and/or $\alpha_v\beta_5$ integrins include endothelial cells, cancer cells, and osteoblasts.

Figure 3:
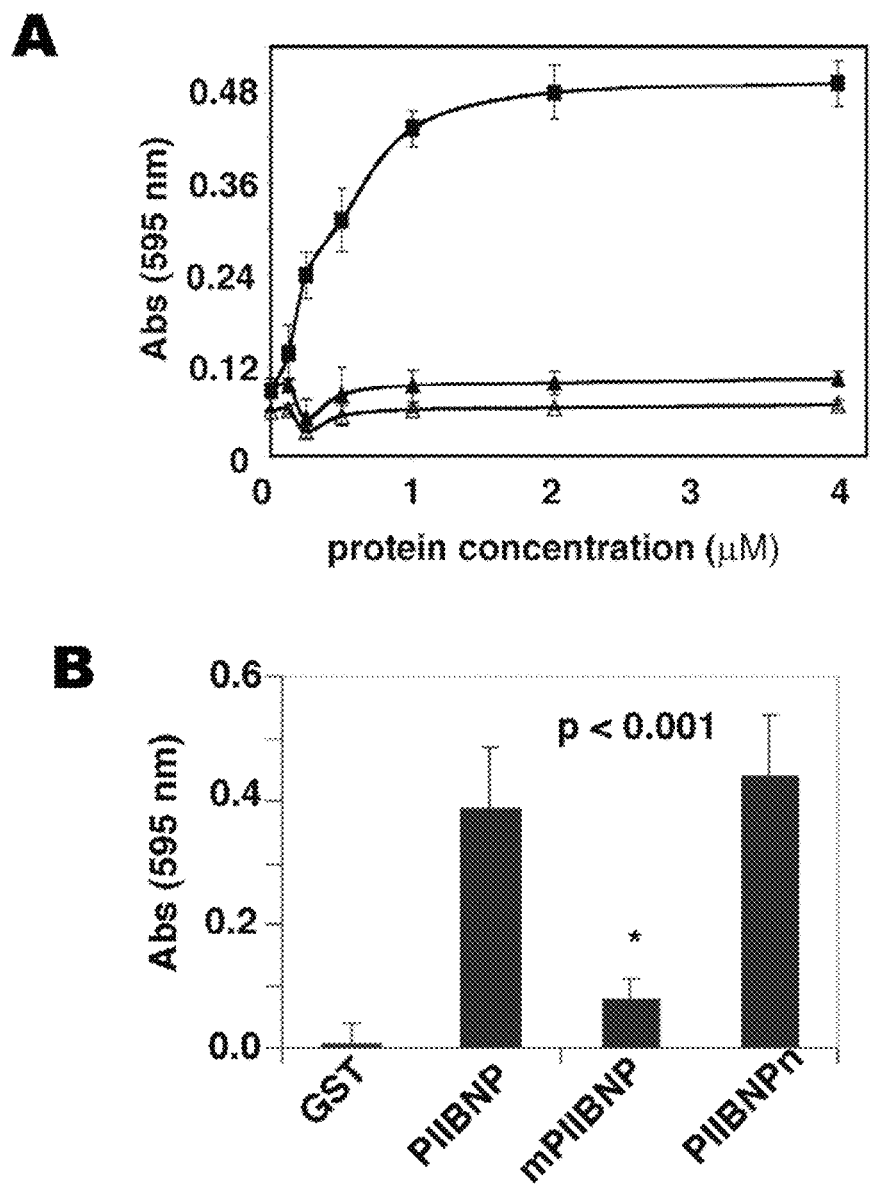
FIG. 3 depicts graphs and images showing integrin-dependent Ch-1 cell adhesion to PIIBNP.
Figure 3:
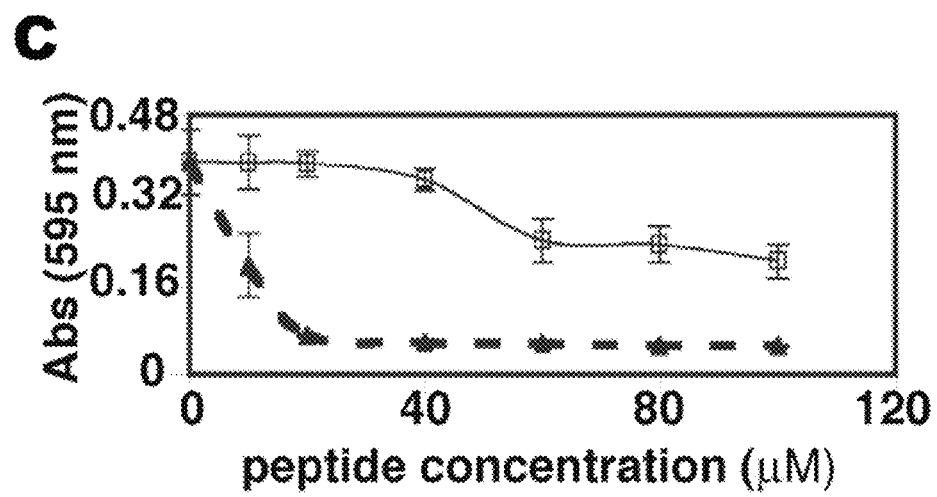
Figure 3:
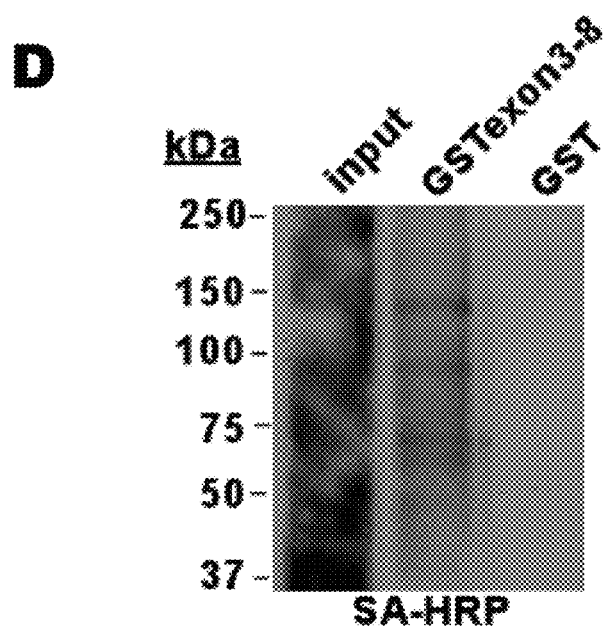
Figure 3:
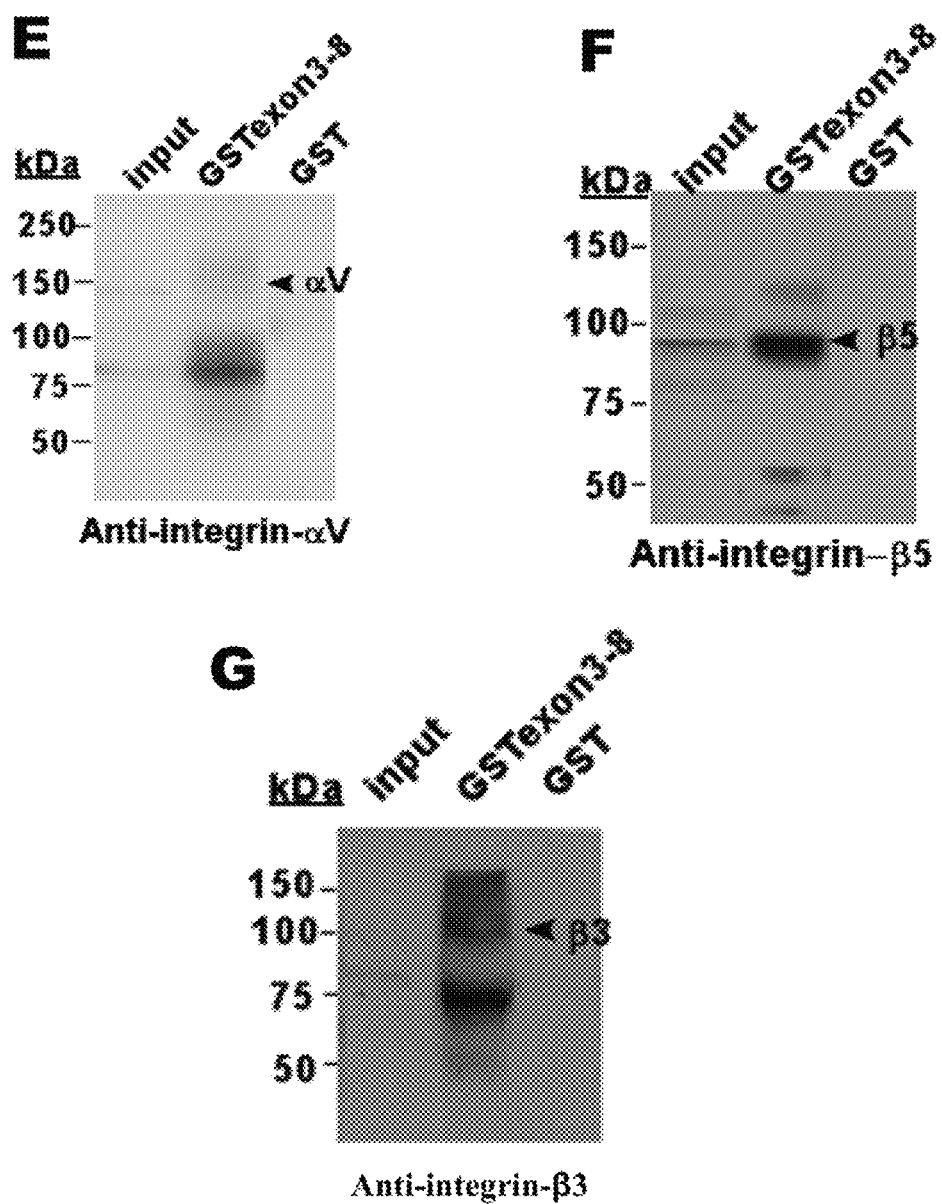
Figure 3:
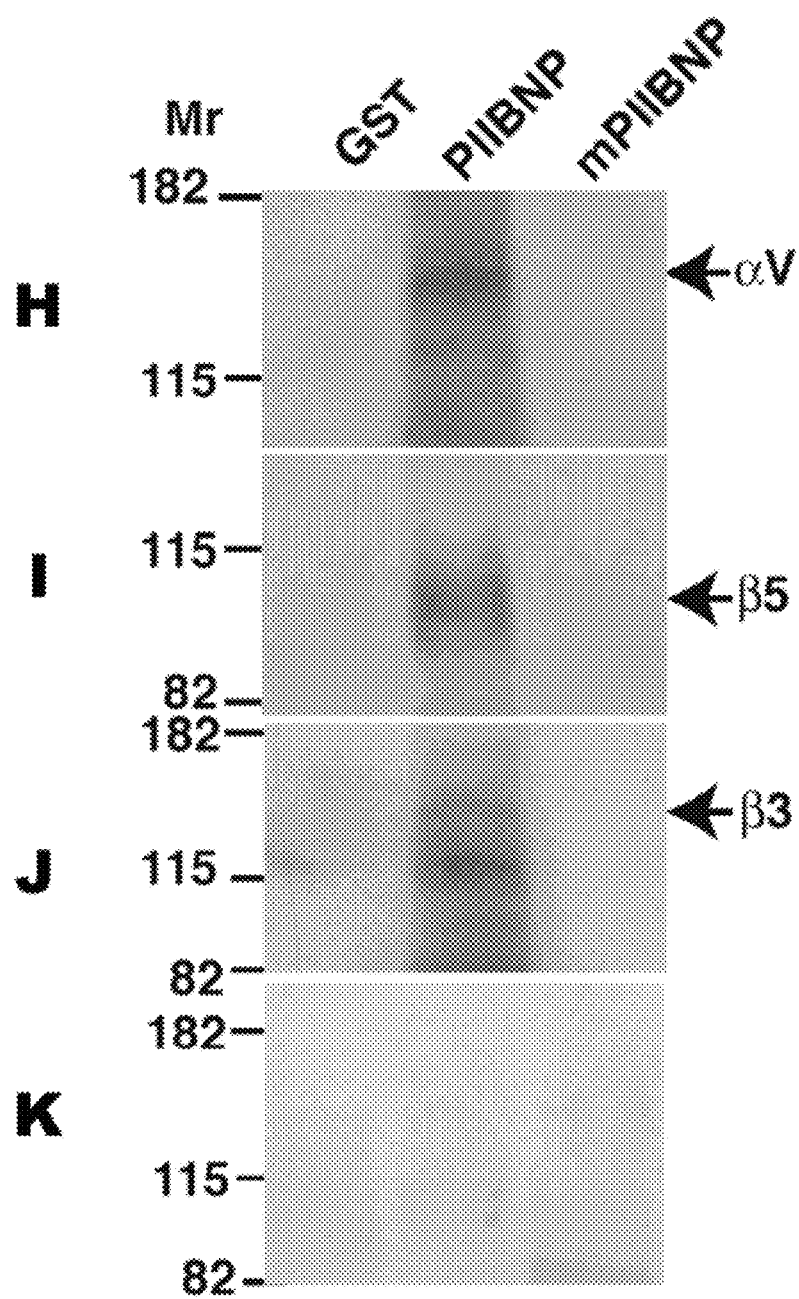
Figure 3:
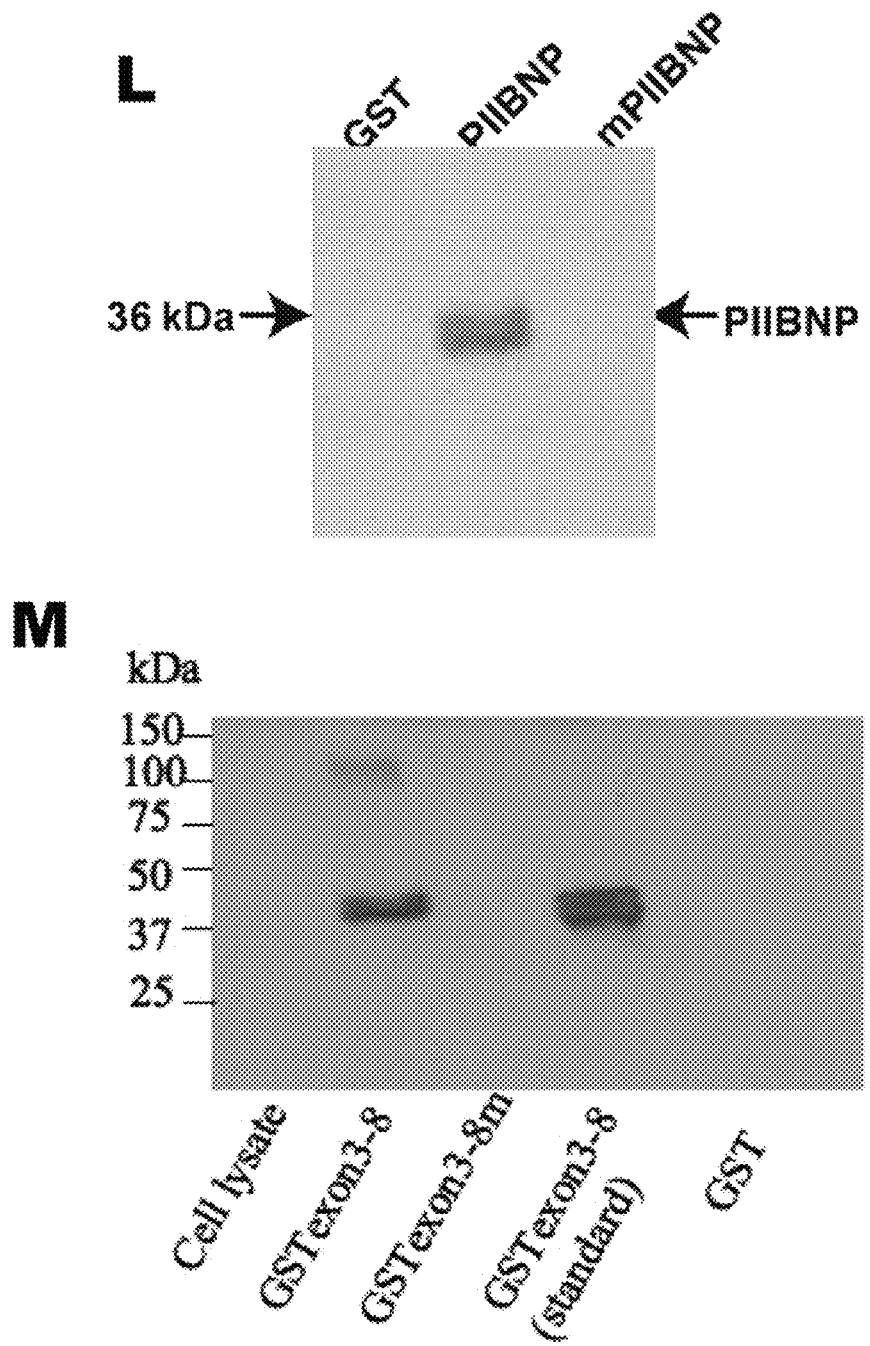
Figure 3N:
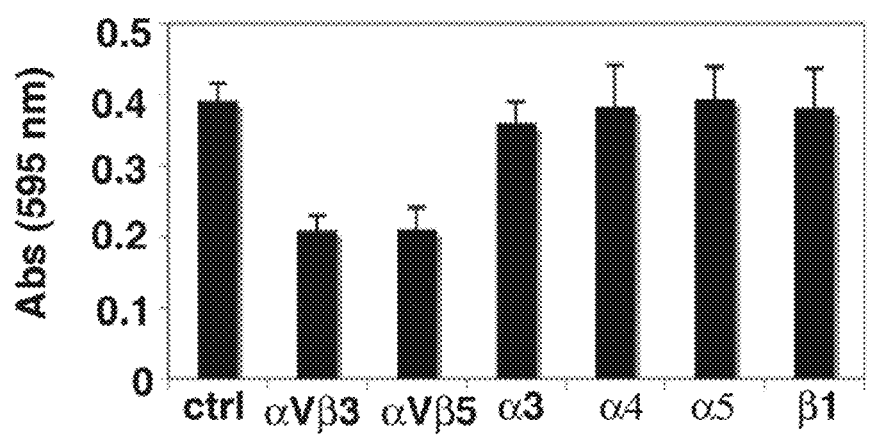
As shown in FIG. 3A, the absorbance at 595 nm represents the number of cells bound to GST (▲), exon 2 (Δ), or PIIBNP (■) (mean±S.E.M. n=8).
FIG. 3B shows the integrin-dependent cell adhesion to PIIBNP is mediated by the RGD motifs. The RGDRGD motif in the PIIBNP protein was mutated to RADRAD (mPIIBNP) and PIIBNPn was obtained by cleavage of GST from a GST-PIIBNP fusion protein with thrombin beads. Cell adhesion to GST, thrombin-cleaved PIIBNP (to remove the GST), PIIBNP and mPIIBNP were assayed. Mutation of the RGD motifs reduced cell adhesion to 18% compared with the PIIBNP (*p<0.001, n=18).
FIG. 3C graphically illustrates that synthetic GRGDNP (▲), but not GRADNP (□) peptides compete and inhibit adhesion.
FIGS. 3D-K demonstrate that PIIBNP binds to $\alpha_V\beta_3$ and $\alpha_V\beta_5$ integrins. Cell adhesion assays show that $\alpha_V$ (FIG. 3E), $\beta_5$ (FIG. 3F) and $\beta_3$ (FIG. 3G) bind to GST-PIIBNP, while GST alone does not (FIG. 3D). Further, mutant PIIBNP, with altered RGD sites, did not bind integrin $\alpha_V$ (FIG. 3H), $\beta_5$ (FIG. 3I) and $\beta_3$ (FIG. 3J), while PIIBNP did. A $\beta_1$ integrin specific antibody did not react with material pulled out by PIIBNP (FIG. 3K). Additionally, PIIBNP was immunoprecipitated with an $\alpha_V$ integrin specific antibody (FIGS. 3L and M), and $\alpha_V\beta_3$ and $\alpha_V\beta_5$ antibodies blocked cell binding of PIIBNP (FIG. 3N) [mean±standard error (S.M.E) n=3)].

Type IIB propeptide (PIIBNP) was shown to adhere to the human chondrosarcoma cell line, Ch-1, while exon 2 alone did not (FIG. 3A). To determine whether PIIBNP binding was integrin-mediated, mutations were introduced to convert the RGDRGD peptide to RADRAD (mPIIBNP). The mPIIBNP did not adhere to Ch-1 cells, while both the GST-PIIBNP and PIIBNPn (devoid of GST) demonstrated strong binding to Ch-1 cells (FIG. 3B). Further evidence of RGD-dependent binding was demonstrated by the ability of synthetic RGD, but not RAD peptides, to compete and inhibit adhesion (FIG. 3C). RGD inhibited 50% at 10 μM whereas RAD inhibited almost 50% at 60 μM. To determine the integrins that were involved in binding to PIIBNP, Ch-1 membrane proteins were labeled with biotin, and PIIBNP was used to isolate the integrin molecules that interacted with the propeptide. The integrins $\alpha_v\beta_3$ and $\alpha_v\beta_5$ were the only integrins identified by immunoreactivity of the PIIBNP-bound proteins on Western blots (FIGS. 3D-K). $\beta_1$, $\alpha_4$, and $\alpha_5$ integrin antibodies did not react with the material pulled out by the PIIBNP (FIG. 3K and data not shown). To confirm the binding of PIIBNP to $\alpha_v$ integrin, a specific $\alpha_v$ antibody was used to immuno-precipitate PIIBNP from Ch-1 cell lysates (FIGS. 3L and M). Further, $\alpha_v\beta_3$ and $\alpha_v\beta_5$ antibodies blocked cell binding of PIIBNP (FIG. 3N).

Methods and Materials

Peptide Production.

Type II collagen $NH_2$-peptides were made using total RNA isolated from 54-d human embryonic tissue. Type II collagen $NH_2$-peptide exon 2 (PIIA-2) and a 315-bp cDNA encoding PIIBNP (exons 3-8) were made as described (Oganesian et al., 1997; Zhu et al., 1999). The cDNAs were cloned into pGEX-4T-2 vector (Clonetech) and GST fusion proteins were expressed using BL21 (DE3) host strains. The recombinant proteins were purified by affinity chromatography. PIIANP (exons 2-8) and mPIIBNP were cloned in the same way for this study. PIIBNP and PIIA-2 proteins were obtained by cleavage of GST from their GST-fusion proteins using a Thrombin CleanCleave Kit (Sigma). The purity of proteins was confirmed by 10% SDS-PAGE.

Cell Adhesion Assay.

Cell adhesion assays were performed using a spectrometric method. A 96-well plate was coated at 4° C. overnight with recombinant proteins. Wells were washed three times with RPMI-1640 medium containing 10% FBS. Ch-1 cells were harvested with limited trypsin digestion and plated at $5\times10^4$ cells per well in RPMI-1640 medium supplemented with 10% FBS for an hours. Proteins were added and incubation continued for 1 hour. The wells were washed three times with pre-warmed PBS to remove non-adherent cells. The adherent cells were fixed with 4% paraformaldehyde in PBS for 10 minutes at room temperature and stained with 0.5% toluidine blue for 5 minutes. The wells were rinsed with water and cells were solubilized with 0.1% SDS. Absorbance at 595 nm was recorded on a SpectraMax plate reader. Synthetic blocking peptides and antibodies to $\alpha_v\beta_3$ and $\alpha_v\beta_5$ integrin were pre-incubated with cells for 15 to 30 mins before they were added onto the wells in the inhibition assays.

Site-Directed Mutagenesis.

Site-directed mutagenesis was performed using a QuikChange Kit to mutate the RGDRGD sequence to RADRAD in PIIBNP. Two mutagenic primers were designed to contain the mutation and anneal to the same sequence on the opposite strands of the plasmid. Two PCR reactions were performed with only one primer in each reaction and pGEX-4T2/exon 3-8 as the template. The two reactions were combined and PCR reaction was continued the reaction for another 9 cycles. The mutated plasmid was confirmed by DNA sequencing and transformed into BL21 (DE3) host stains to express mutated PIIBNP (mPIIBNP).

Integrin $\alpha_v$ Immunoprecipitation.

Ch-1 cells were lysed in lysis buffer (50 mM Hepes-KOH [pH 7.4]; 150 mM NaCl; 1% Triton X-100; 10% glycerol; 1 mM EGTA; 1 mM EDTA; 10 mM sodium pyrophosphate; 100 mM sodium fluoride; 0.2 mM sodium orthovanadate; supplemented with the proteinase inhibitors cocktail (Sigma) overnight at 4° C. Cell homogenates were then mixed with GST, PIIBNP, or mPIIBNP and incubated for 1 hours at room temperature. Protein A agarose (Sigma) previously bound with integrin $\alpha_v$ antibody was incubated with cell homogenate mixture for 4 h at 4° C. with gentle shaking. After washing (5 mins.×3), the precipitated material was analyzed by SDS-PAGE and detected with chicken anti PIIBNP antibody.

Immunoblotting.

Western blotting was performed as described (7). Blots were probed with the following primary antibodies: rabbit anti $\alpha_v, \alpha_2, \alpha_3, \alpha_5, \beta_1, \beta_3, \beta_5$ integrin and goat anti actin (Saint Cruz), chicken anti PIIBNP antiserium, and mouse anti exon 2 antiserum.

Cell Surface labeling and GST Pull-Down Assay.

Ch-1 cells were incubated with EZ-link Sulfo-NHS-Biotin reagent for 30 mins. according to the product instruction (Sigma). After 3 washes with 0.1 M glycine in PBS, the cells were lysed with a lysis buffer described above. The lysate was incubated with glutathione derivatized agarose beads previously bound with GST, PIIANP, PIIBNP or mPIIBNP for 1 hr. at RT. After washing, the bound proteins were separated by SDS-PAGE and transferred to a nylon membrane that was subsequently blocked with 5% non-fat dry milk for 1 hr. The membrane was washed and incubated with antibodies and then incubated with a secondary antibody coupled to horseradish peroxidase. The antibody complex was visualized by enhanced chemiluminescence.

Antibodies.

Monoclonal antibodies used for blocking experiments were: mouse anti $\alpha_v\beta_3$ and $\alpha_v\beta_5$ integrins (Chemicon). Polyclonal antibodies for immunohistochemistry and western blotting were rabbit anti human $\alpha_v, \alpha_2, \alpha_3, \alpha_5, \beta_1, \beta_3, \beta_5$ integrin, goat anti human actin (Santa Cruz), mouse anti exon 2, rabbit anti GST exon 2, and chicken anti PIIBNP (antiserum made in our lab).

Cell Culture.

Human Chondrosarcoma cell line (Ch-1) was isolated from a portion of chondrosarcoma tumor (Chansky et al., J Orthop Res. (1998) 16(5):521-30). The Ch-1 cell line was maintained in RPMI-1640 supplemented with 10% FBS and at 37° C. in a humidified, 5% $CO_2$ atmosphere.

Example 3

Type IIB Induces Cell Death

The $\alpha_v\beta_3$ and $\alpha_v\beta_5$ integrins are key regulators of adhesion and signaling in numerous biological processes, including tumor cell migration and metastasis, and angiogenesis. Interaction with $\alpha_v\beta_3$ and $\alpha_v\beta_5$ integrins likely affects these processes. As such, the functional outcome of the interaction between the collagen $NH_2$-propeptide and integrins was analyzed.

Figure 4:
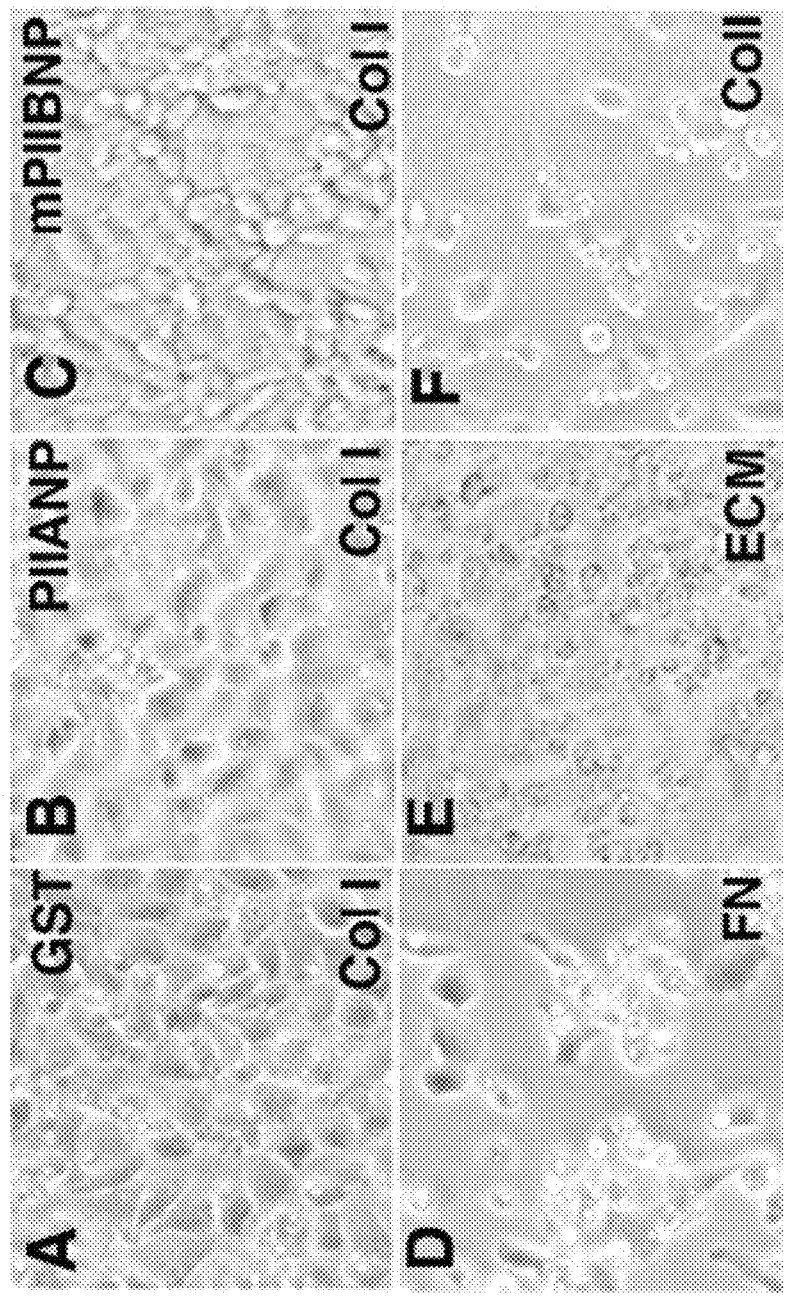
FIG. 4 depicts a series of micrographs and a graph showing PIIBNP induced cell death in Ch-1, MDA-MB231, and HeLa cells in a substrate-independent manner. Culture plates were coated with type I collagen (FIGS. 4A, B, C and F), fibronectin (FIG. 4D) and EMC Matrigel (FIG. 4E). Ch-1 cells were incubated with 0.8 μM of GST (FIG. 4A) PIIANP (FIG. 4B) mPIIBNP (FIG. 4C) or PIIBNP (FIGS. 4D-F) in serum free medium for 24 hrs. Quantification of cell survival (FIG. 4G) showed PIIBNP, but not PIIANP, induced cell death. The assays were performed in fibronectin (black), ECM Matrigel (gray), or type I collagen (white) coated plates. The values represent means±S.E.M. for three independent assays. Cell survival assays were performed on human chondrocytes (FIGS. 4H and K), MDA-MB231 cells (FIGS. 4 I and L), and HeLa 229 cells (FIGS. 4J and M). PIIBNP induced cell death of HeLa 229 cells (>80%, FIG. 4M) and, MDA-MB231 cells (>70%, FIG. 4L), but did not induce cell death in normal human articular chondrocytes (FIG. 4K).
Figure 4G:
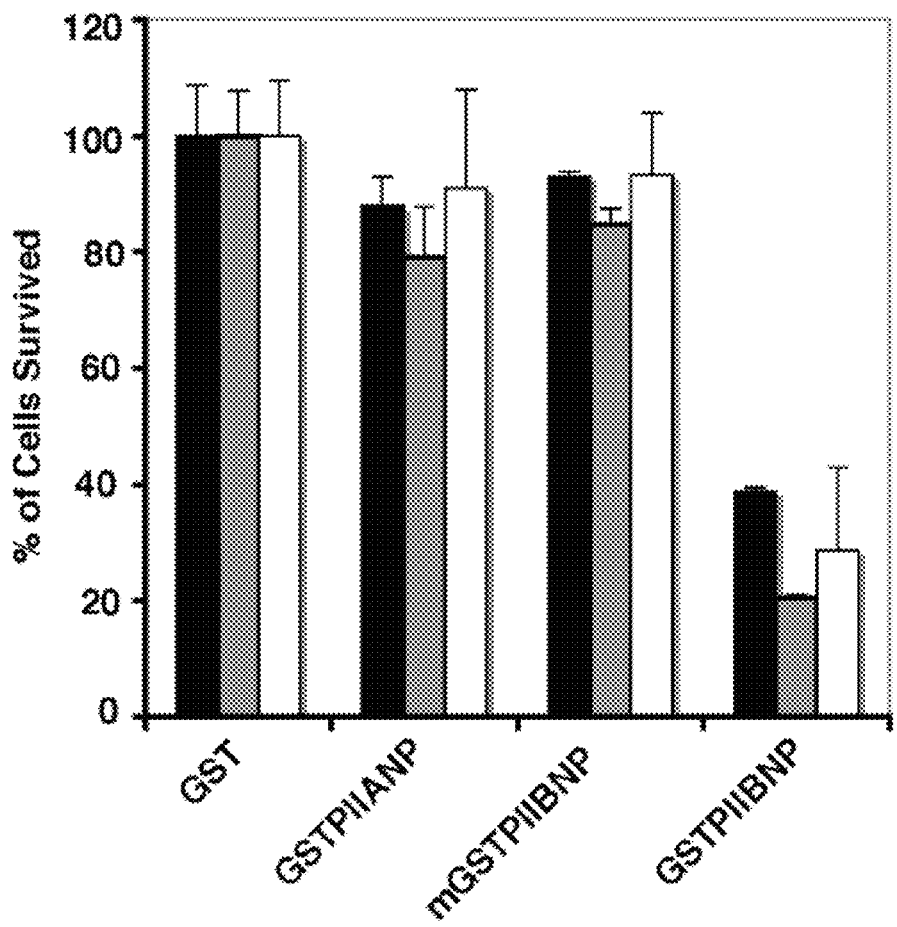
Figure 4:
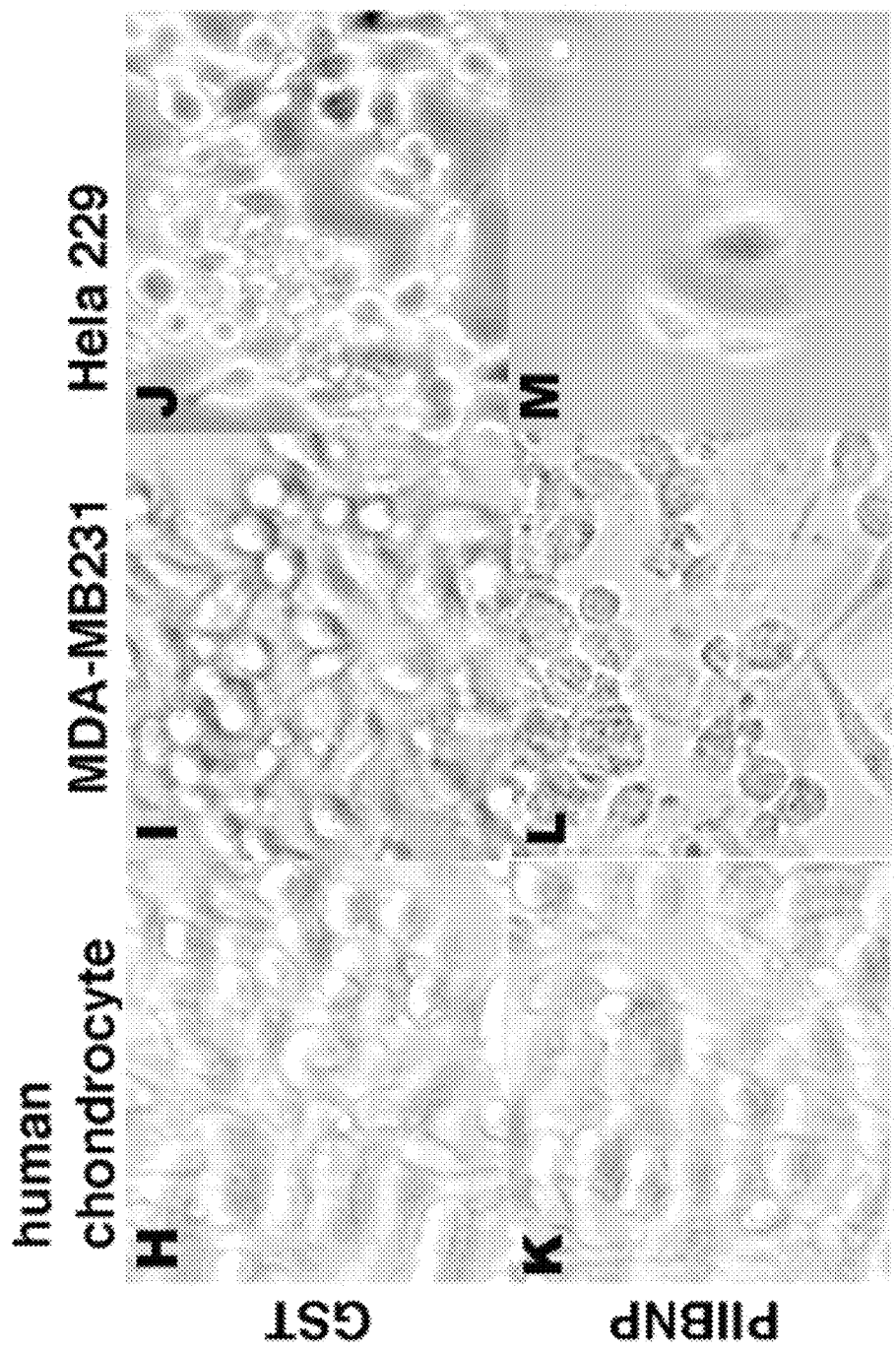

The addition of PIIBNP to Ch-1 cell cultures resulted in cell death in a concentration and time-dependent manner. As an assay for cell death, the number of cells present in the culture dish at specific time points was determined by counting. In the presence of 0.8 μM PIIBNP, cell survival ranged between 20-30%. The induction of cell death was not dependent on the extracellular matrix substrate (FIGS. 4A-F). Whether cultured on type I collagen (FIGS. 4A-C and F), fibronectin (FIG. 4D) or Matrigel (FIG. 4E), PIIBNP was able to induce cell death in Ch-1 cells (FIGS. 4D-F). Cells plated in the presence of serum only were also killed (data not shown). The ability of PIIBNP to induce cell death is independent of extracellular matrix ligand, which indicates that this is not detachment-mediated cell death. The time frame of induction (16-24 hours) also is inconsistent with detachment-mediated cell death. Furthermore, PIIANP (FIGS. 4B and G), mPIIBNP (FIGS. 4C and G), or GST alone (FIGS. 4A and G) did not induce cell death in Ch-1 cells. The inability of the PIIANP splice form to elicit cell death suggests that the presence of the cysteine-rich exon 2 provides the Type IIA $NH_2$ propeptide with a biological function distinct from Type IIB.

In order to determine whether this property of PIIBNP could be extended to cancer cells other than chondrosarcoma, two additional cell lines that express $\alpha_v\beta_3$ and $\alpha_v\beta_5$ were used: HeLa cells derived from a cervical carcinoma, and MDA-MB231 cells derived from breast cancer. PIIBNP induced cell death in both HeLa (FIGS. 4J and M; 20% survival) and the MDA cells (FIGS. 4I and L; 30% cell survival).

Cartilage is avascular and resistant to tumor invasion. The molecular mechanism underlying these characteristics of cartilage has been elusive for nearly 50 years. By virtue of the expression pattern of PIIBNP, highest during cartilage formation, and the ability of PIIBNP to recognize $\alpha_v\beta_3$ and $\alpha_v\beta_5$ integrins found on endothelial and osteoclast type cells, PIIBNP is a candidate for the molecular mechanism by which cartilage remains avascular and intact. Therefore, it was of interest to analyze the susceptibility of normal human articular chondrocytes to the effect of PIIBNP. Normal human articular chondrocytes were isolated from two sources, a child and an adult, and cultured in high-density monolayers. PIIBNP did not induce cell death in normal chondrocytes (FIGS. 4H and K), thus indicating that in vivo, normal chondrocytes are likely protected from this mechanism of cell death.

Figure 5:
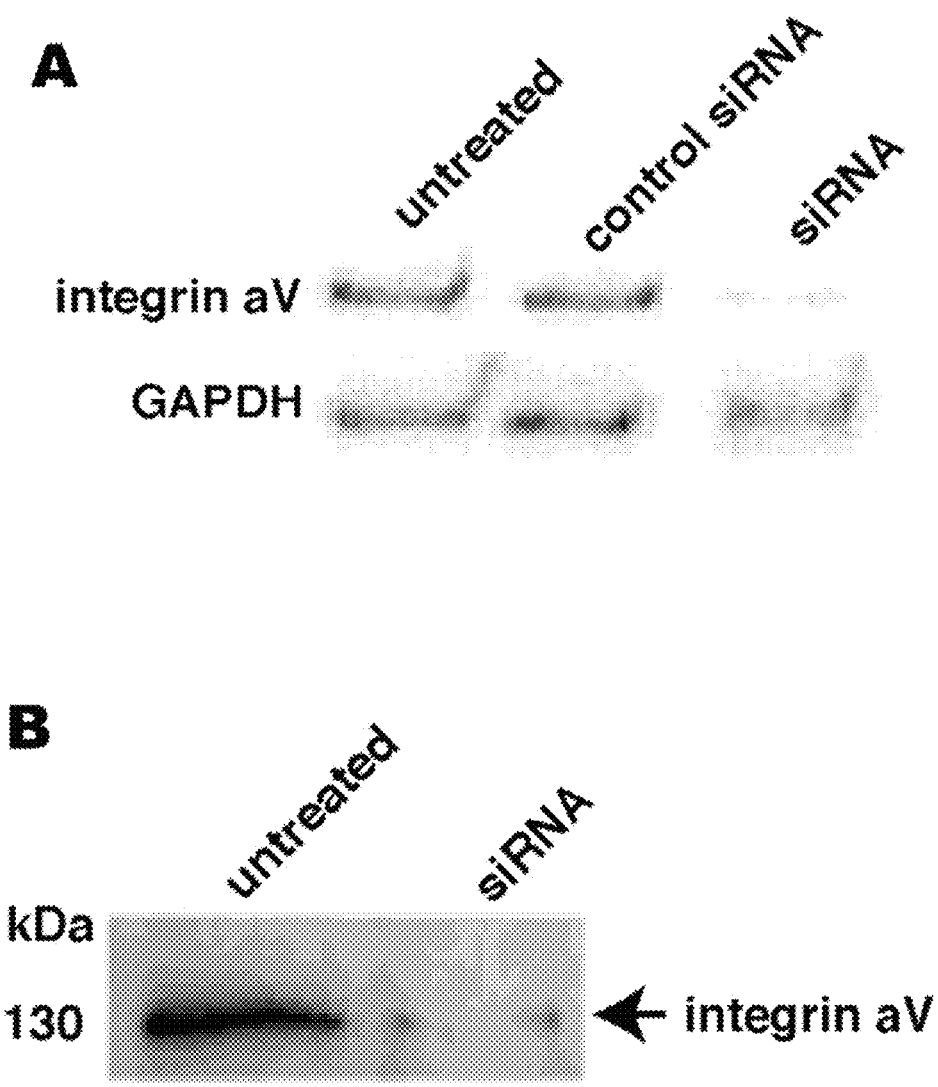
FIG. 5 depicts a series of photographs showing that PIIBNP induces cell death in an integrin $\alpha_V$ dependent manner. Ch-1 cells, treated with synthetic siRNA to knock down integrin $\alpha_V$, exhibited a reduction of integrin $\alpha_V$ that was more than 70% lower at the RNA (FIG. 5A) and protein (FIG. 5B) levels. The untreated and siRNA treated Ch-1 cells were plated in plates coated with type I collagen and incubated with 0.8 μM of GST (FIGS. 5D and I), PIIBNP (FIGS. 5E and J), mPIIBNP (FIGS. 5F and K) or PIIANP (FIGS. 5G and L) in a serum-free medium for 24 hrs. PIIBNP did not induce cell death in the siRNA-treated Ch-1 cells.
Figure 5:
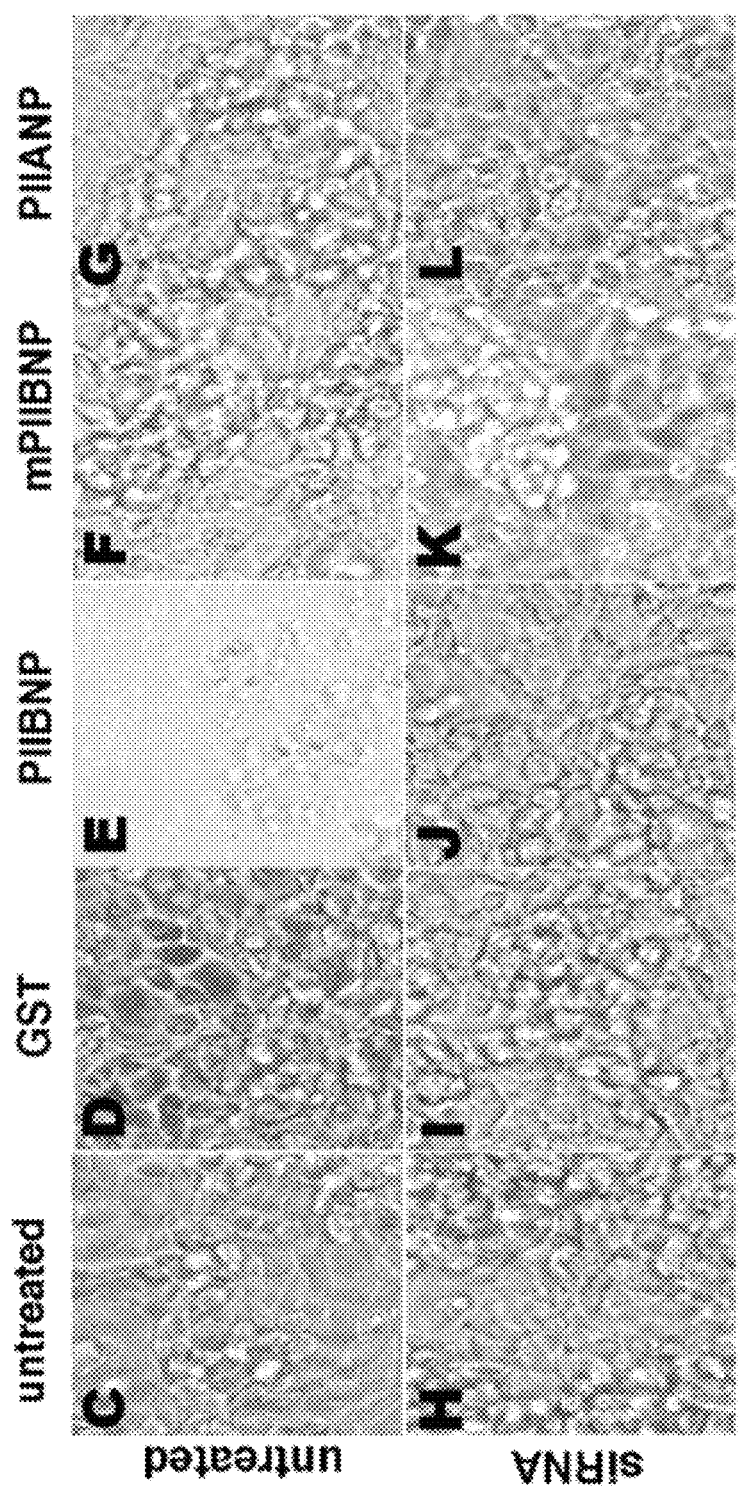
Figure 5M:
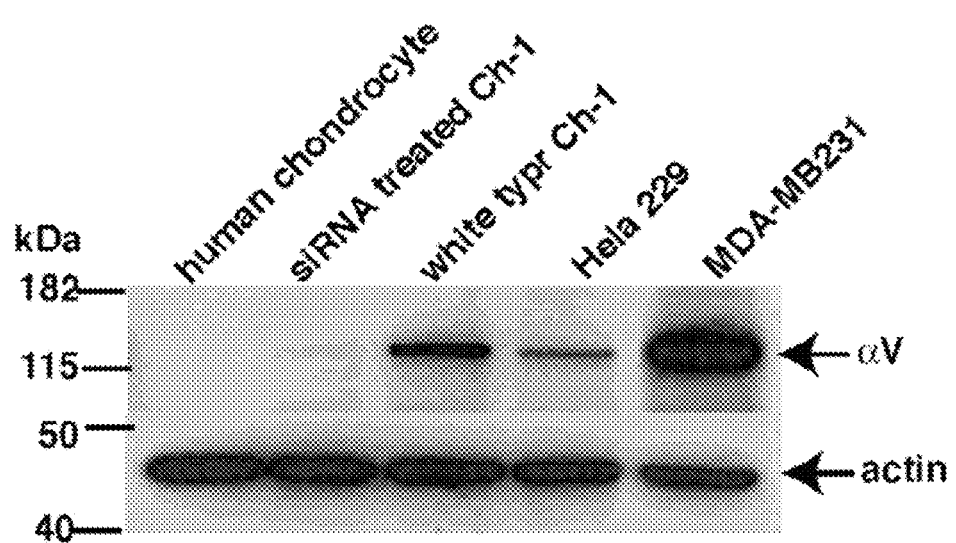
FIG. 5M shows western blot analysis of integrin $\alpha_V$ protein expression in human chondrocyte cells, $\alpha_V$ siRNA treated Ch-1 cells, wild type Ch-1 cells, HeLa 29 cells, and MDA-MB231 cells.

Together, these results strongly suggested that PIIBNP-mediated cell death required the RGD sequence and the cellular integrins $\alpha_V\beta_3$ or $\alpha_V\beta_5$. Three approaches were taken to confirm the requirement for integrin binding. First, $\alpha_V$ integrin expression, common to both $\alpha_V\beta_3$ and $\alpha_V\beta_5$, was blocked by siRNA in the Ch-1 cells. FIGS. 5A and 5B show the reduced $\alpha_V$ mRNA and protein levels, respectively. In cells that no longer expressed detectable $\alpha_V$, PIIBNP was not able to induce cell death (FIGS. 5E and J). Secondly, it was of interest to determine whether the ability to cause cell death correlated with the cellular expression of $\alpha_V\beta_3$ and $\alpha_V\beta_5$ integrins. In order to coordinate $\alpha_V$ expression with cell death, cell lysates were probed for the presence of the integrin $\alpha_V$. Western blot analyses of Ch-1, HeLa, and MDA confirmed that the expression of $\alpha_V$ was positively correlated with the ability of PIIBNP to kill the cells (FIG. 5M). Normal chondrocytes did not express $\alpha_V$, thus they were protected from this mechanism of cell death. (FIG. 5M).

Materials and Methods

Cell Culture.

Human Chondrosarcoma cell line (Ch-1) was isolated from a portion of chondrosarcoma tumor. The Ch-1 cell line was maintained in RPMI-1640 supplemented with 10% FBS and at 37° C. in a humidified, 5% $CO_2$ atmosphere. Human chondrocytes were obtained from Dr. Davis Adkisson (ISTO Technologies, St. Louis) or isolated from macroscopically intact tissue obtained from total joint arthroplasty as described (Bassleer et al., 1998). HeLa 229 cells and MDA-MB 231 cell lines were provided by Dr. Kathy Weilbaecher (Washington University) and were cultured in RPMI medium supplemented with 10% FBS. HUVEC cells were a gift from Dr. William Frazier (Washington University) and were cultured in M199 Earle's medium with 10 units/ml of penicillin, 5 μg/ml streptomycin and 0.25 μg/ml Fungizone supplemented with 10% FBS, 0.1 mg/ml L-glutamine, 25 mM Hepes, 16 units/ml of heparin (Sigma) and 0.1 mg/ml endothelial cell mitogen (Biochemical Technologies).

Detection of Cell Death.

Cells were cultured to confluence in a 24-well plate pre-coated with type I collagen, fibronectin (Sigma), and ECM Matrigel (Becton Dickinson). Proteins in serum-free medium were added to the cells. Cells were monitored by light microscopy and images were digitally photographed using a Q capture Retiga 2000R camera. Quantification of cells remaining in the well was performed by washing with PBS for three times, fixing with 4% paraformaldehyde. The cells per field (×400) were counted for three field per well (3 wells per measurement). The mean number and standard deviation (SD) were calculated.

SiRNA Interference.

Ch-1 cells were grown to 60-80% confluence in 6 well plates in Opti-Mem medium (Invitrogen) without antibiotics and serum. A reported method (6) is used in the design of siRNAs, sense and antisense oligonucleotides. The final concentration of oligonucleotides was 0.05 μM. Transfection was performed using a lipofectamine kit (InVitrogen). Half of the wells were stimulated with 200 ng/ml PMA (phorbol 12-myristate 13-acetate) after 4 hours incubation with oligonucleotides. Total RNA was collected via the TriZol method after incubation for 44 hours. 1 μg of total RNA was reverse transcribed with Superscript RT II in a 40 μl volume. 5 μl of the cDNA were used for semiquantitative $[\alpha^{32}P]dCTP$ PCR for alpha V integrin and GAPDH: the former amplified for 26 cycles and the latter for 20 cycles. Samples were run on 6% SDS-PAGE, dried, and exposed to Storm 840 phosphor imager (Amersham Pharmacia Biotech). Bands were quantified with Image Quant software.

Example 4

Type IIB Inhibits Angiogenesis In Vitro

Endothelial cells, particularly in the tumor vasculature, express high levels of $\alpha_V\beta_3$ and $\alpha_V\beta_5$. In light of the requirement of $\alpha_V\beta_3$ and $\alpha_V\beta_5$ for cell death by PIIBNP, and the lack of blood vessels in normal cartilage, it was of interest to determine whether PIIBNP could function as an inhibitor of angiogenesis. Two well-accepted assays were applied to determine the ability of PIIBNP to inhibit angiogenesis: cell tube formation in human umbilical vein endothelial cells (HUVEC) and the rat aortic ring endothelial cell outgrowth bioassay.

Figure 6:
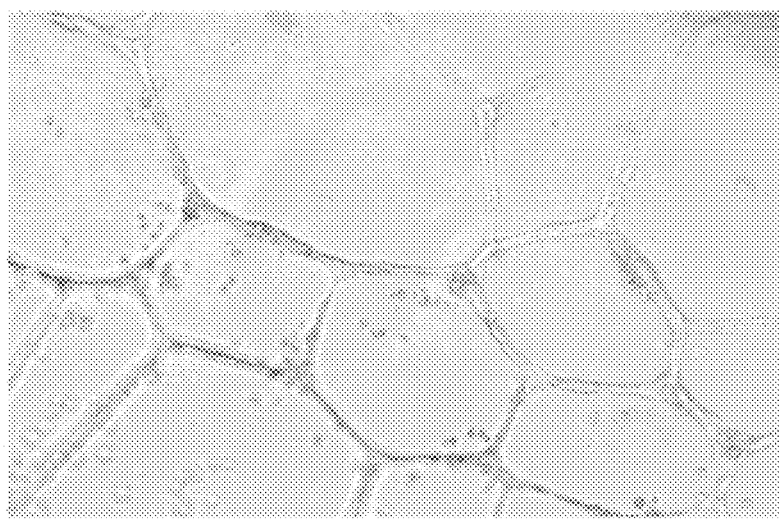
FIG. 6 depicts photographs and graphs showing that PIIBNP inhibits angiogenesis. Specifically, FIGS. 6A and B demonstrate the inhibitory effect of PIIBNP on tube formation in HUVEC cells plated on Matrigel-coated plates in presence of 0.8 μM GST (FIG. 6A) or PIIBNP (FIG. 6B). Quantification of tube formation was calculated based on branch points per field of view (FIG. 6C) for each treatment ranging from 0.1 μM to 10 μM of PIIBNP.
Figure 6:
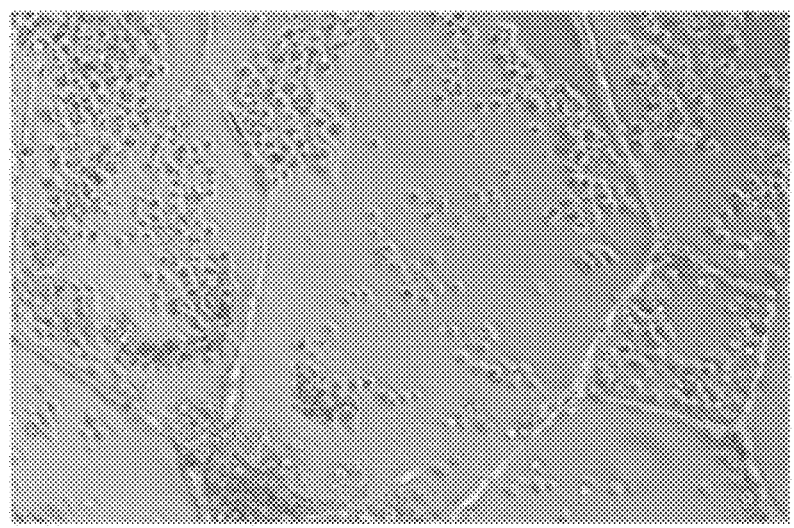
Figure 6C:
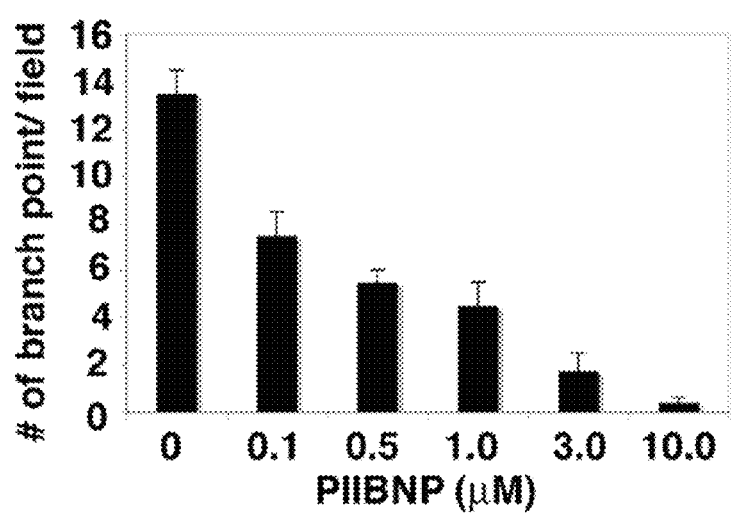
FIG. 6D shows that PIIBNP, incubated with HUVEC cells (60 hrs. 37° C.), caused cell death in a concentration-dependent manner (■). GST (▲) and PIIANP (●) had no effect on the cells.
Figure 6D:
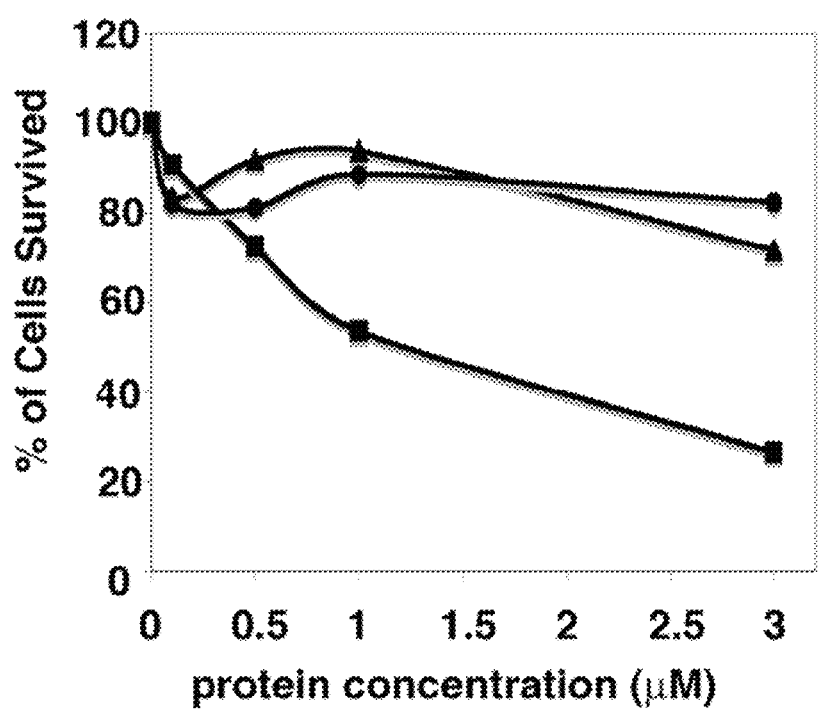
Figure 8A:
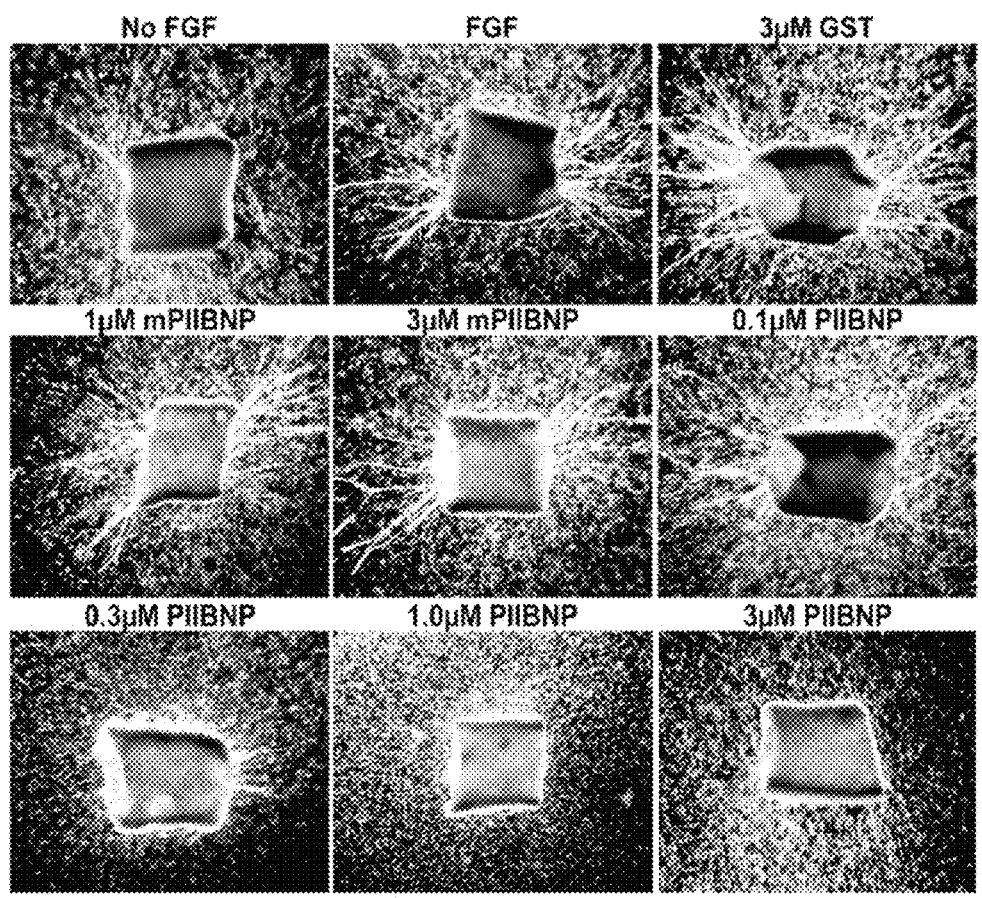
(FIG. 8A) The length of microvessels was measured and total length for each measurement was added (FIG. 8B). PIIBNP inhibited aortic ring formation, with an $IC_{50}$ of less than 0.1 μM.
Figure 8B:
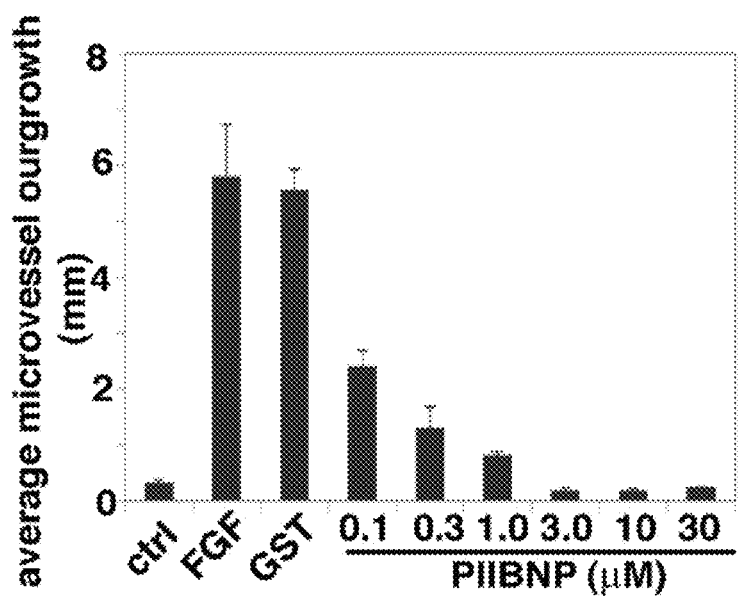
FIG. 8 depicts a graph and photograph showing rat aortic ring formation. Angiogenesis was assayed by culturing rings of rat aorta in three-dimensional collagen gel. The culture was performed at 37° C. in a humidified environment for a week in the presence FGF and mPIIBNP or PIIBNP (0.1 to 3 mM). The microvessel outgrowth was examined and visualized every second day with an Olympus microscope. The pictures were taken before the measurement of the microvessels.

Using the cell tube formation in HUVECs, PIIBNP (FIG. 6B), but not GST alone (FIG. 6B), was able to inhibit the formation of tubes in a dose-dependent manner (FIG. 6C). mPIIBNP was also not able to inhibit tube formation (data not shown). As a second test for angiogenesis, we tested the ability of PIIBNP to inhibit outgrowth of endogenous endothelial cells from freshly isolated rat aorta. PIIBNP, but not GST alone, was able to inhibit endothelial outgrowth in a concentration dependent manner (FIG. 6D). In order to determine whether PIIBNP caused endothelial cell death, the number of HUVEC cells present after incubation with PIIBNP was determined (FIGS. 6E and 8). Tube formation was inhibited by 50% with 0.1 μM PIIBNP, with no cell death. At higher concentrations of PIIBNP, cell death was induced. These results indicate that PIIBNP was likely inhibiting migration at the lower concentrations. PIIBNP can inhibit migration of Ch-1 cells (data not shown). Consequently, PIIBNP can inhibit angiogenesis in a cell line and in endogenous endothelial cells mediated by integrins $\alpha_V\beta_3$ and $\alpha_V\beta_5$.

Materials and Methods

Tube Formation Assay.

The tube formation assay using HUVEC cells was performed as described with some modification. Briefly, a suspension of $7.5 \times 10^4$ cells/well in complete medium was seeded into a Matrigel-coated 24-well plate in the presence of recombinant PIIBNP or GST (0-10 μM). The formation of tubes was evaluated using light microscopy and quantification was performed using a Q Capture Pro imaging software. Branch points per field were counted from three fields for each treatment.

Aortic Ring Formation Assay.

Angiogenesis was assayed by culturing rings of rat aorta in three-dimensional collagen gels as reported. The cultures were kept at 37° C. in a humidified environment for a week in the presence of FGF and GST or PIIBNP (0.1-10 μM). The microvessel outgrowth was examined every second day with an Olympus microscope. The length of microvessels was measured and total length for each measurement was added.

Example 5

Internalization of Type IIA and Type IIB Propeptides

The $\alpha_V\beta_3$ and $\alpha_V\beta_5$ integrins have been shown to play a role in endocytosis. Specifically, the $\alpha_V\beta_3$ and $\alpha_V\beta_5$ integrins have been found to participate in endocytosis of vitronectin and internalization of shed outer rod segments in the retinal pigmented epithelium. Based on these observations, it was of interest to determine if Type II collagen amino propeptides could be internalized following binding to $\alpha_v\beta_3$ and $\alpha_v\beta_5$ integrins.

Figure 7:
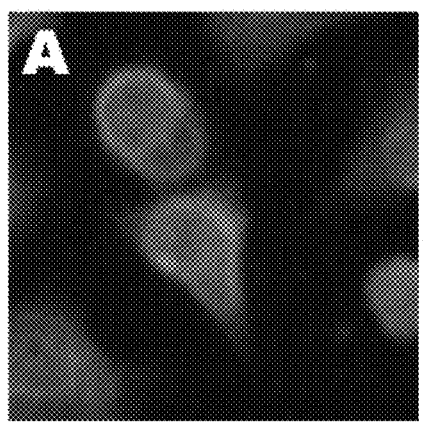
FIG. 7 depicts photomicrographs showing cell internalization of Type II collagen amino propeptides. While PIIBNP (FIG. 7B) is internalized into the cell, PIIANP is not (FIG. 7A). PIIBNP colocalized with actin filaments within 30 minutes of exposure to the cell (FIG. 7D), while PIIANP does not (FIG. 7C). Following 2 hours of exposure to a cell PIIBNP colocalized with the nucleus (FIG. 7E).
Figure 7:
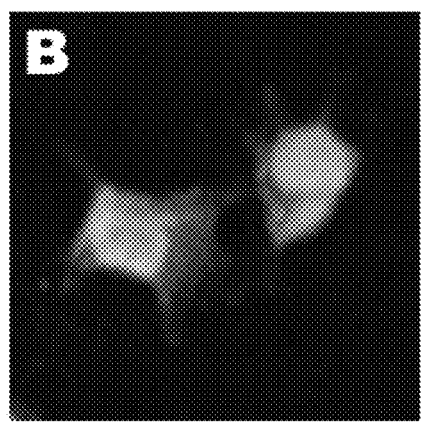
Figure 7:
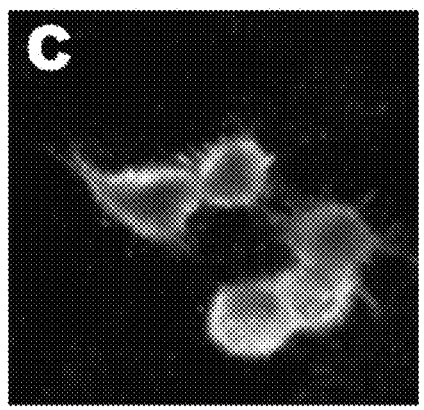
Figure 7:
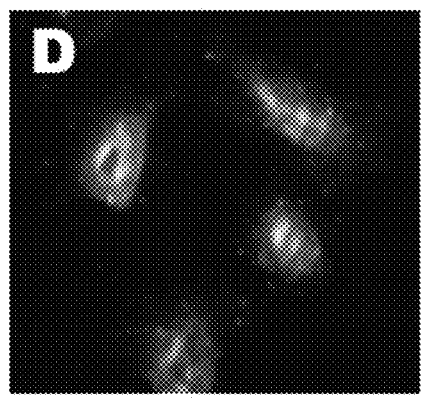
Figure 7:
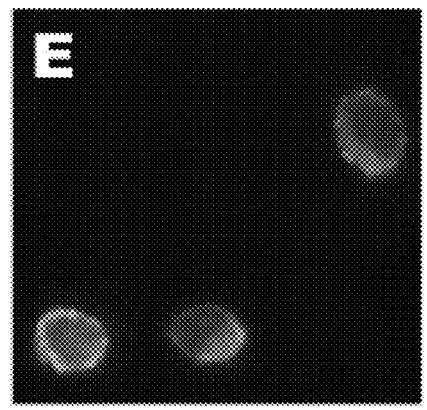

Ch-1 cells exposed to GST-PIIBNP and GST-PIIANP were immunostained with immunospecific antibodies. While PIIBNP was internalized into cells (FIG. 7B), PIIANP was not (FIG. 7A). After 30 minutes of exposure to the cells, PIIBNP colocalized with actin filaments. Nearly 2 hours after exposure to the cells, PIIBNP had localized to the nucleus. The internalization of PIIBNP may be exploited to target exogenous agents to cells expressing $\alpha_v\beta_3$ and $\alpha_v\beta_5$ integrins.

Example 6

In Vivo Mouse Cornea Angiogenesis Inhibition Assay

FGF containing PolyHEMA pellets were implanted into the corneas of 6 week old Balb/c mice. The mice received osmotic pumps containing a number of proteins to measure the ability of each protein to inhibit angiogenesis. After one week the mice were sacrificed and angiogenesis was quantified based on the total vessel length seen from fluorescently labeled vessels.

To prepare a FGF Pellet (67 ng/quarter pellet) PBS (1 µl of 1×PBS pH 7.4), sucralfate (Sigma, #50652) (1 µL of a 100 mg/mL suspension of sucralfate), Human FGF-2 (Peprotech, 100-18B)(1 µL of 3.2 mg/mL FGF-2), and poly-hema (poly (2-hydroxyethyl methacrylate), Sigma, P3932)(3 µL of 250 mg/mL poly-hema) were combined. Pellets (0.5 µL) were prepped on parafilm, air dried for 10-20 mins, and divided into quarters. The resulting pellets were sealed with parafilm and stored at −20° C. until needed.

To implant the pellet, a mouse was injected with Ketamine/Xylazine (about 0.1 mg KX/gram mouse, IP injection). When the mouse was non-responsive to pain stimuli, a Beaver blade (or #15 scalpel blade), was used to carefully score the cornea several times, with the incisions halfway through the cornea. A number 11 scalpel blade was used to carefully open a pocket in the corneal incision. Using the micro dissecting knife (Roboz, RS-6270), a pocket large enough for the insertion of the pellet was created. A pellet was inserted fully into the pocket, and antibiotic ointment was applied to both eyes.

Immediately after the pellet is implanted a small section of fur is shaved from the lower back of the mouse. The area is cleaned with ethanol and betadine. A 0.1 cc dose of ketoprofen (1 mg/ml) is injected (IP injection on opposite side that ketamine was injected). Using sterile forceps and sterile surgical scissors a small incision is made and widened to approximately 2 cm in length. A sterile hemostat is inserted into the incision and used to deepen and widen a subcutaneous pocket. The pump is inserted into the pocket, flow regulator end first, and gently pushed towards the scapula. The flaps of skin are pinched together with sterile forceps and stapled to bind the wound.

Figure 9:
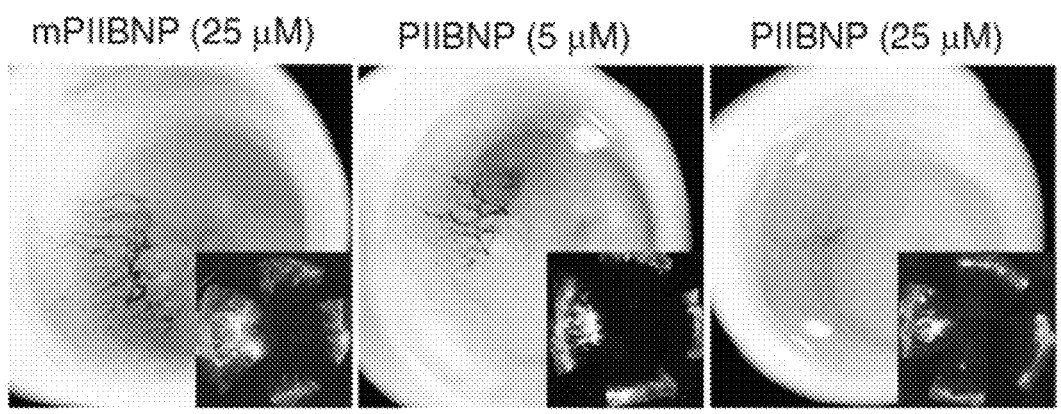
FIG. 9 depicts pictures and a graph showing that PIIBNP inhibits FGF induced mouse cornea neovascularization. PolyHEMA pellets containing FGF were prepared and implanted into the mouse corneas of 6 weeks old Balb/c mice. The mice received osmotic pumps containing PIIBNP or mPIIBNP to measure the ability of the proteins to inhibit angiogenesis. After one week, the mice were sacrificed and angiogenesis was quantified based on the total vessel length seen from fluorescently labeled vessels.
Figure 9:
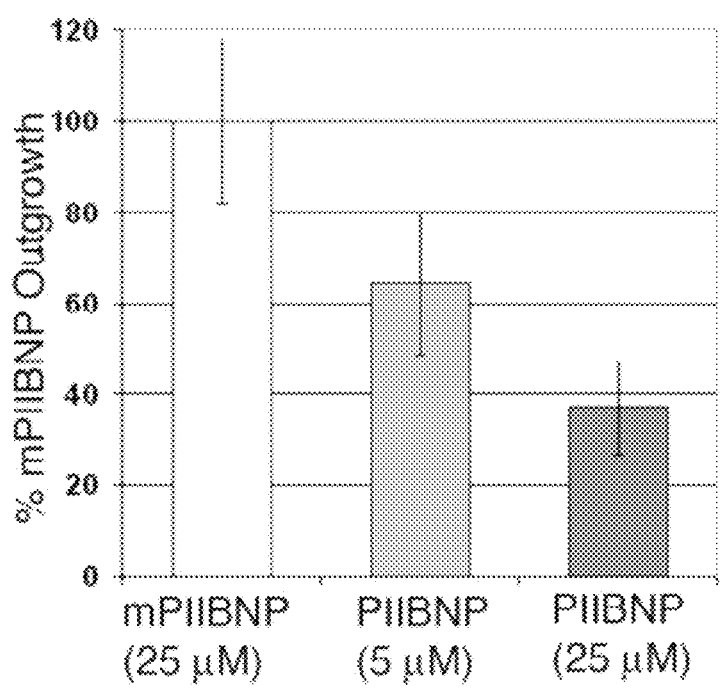

After one week the mice are injected with same amount of Ketamine given during the implantation procedure. Images are taken on dissecting scope (Nikon, SMZ1500). Retroorbital injections of 0.1 cc FITC-Dextran (50 mg/ml) (Sigma, #FD2000S-1G) are administered in the left eye (opposite eye of pellet implantation), and the FITC-Dextran is allowed to circulate through mouse for five minutes. The mouse is sacrificed in a $CO_2$, and the right eye is removed using sterile scissors and immediately placed into PBS. Images of the eye are taken in the dish with PBS. Using forceps and a number 10 blade the eye is punctured and all tissues are removed from the cornea, being very careful not to damage the corneal tissue or limbic vessel. Any remaining tissues will show up when the cornea is mounted and viewed with fluorescence. It is therefore important to remove all tissues outside of the limbic vessel and all iris tissues. Small incisions are made in the cornea at 4 points to help flatten the cornea when mounted on a slide. The prepared cornea is fixed in 4% PFA for 10 mins and mounted in 100% glycerol. Angiogenesis is measured by total vessel outgrowth based on the fluorescently stained blood vessels using Metamorph software (FIG. 9).

For more details, see Kenyon et al., Invest Ophthalmol V is Sci 1996; 37:1625-32; Wu et al., Mol Vis. 2005 Jan. 13; 11:28-35; and Dell et al., IOVS, May 2006, Vol. 47, No. 5.

Importantly, these data show that PIIBNP inhibits angiogenesis in vivo with no apparent toxicity.

Example 7

Inducing Osteoclast Death

Figure 10:
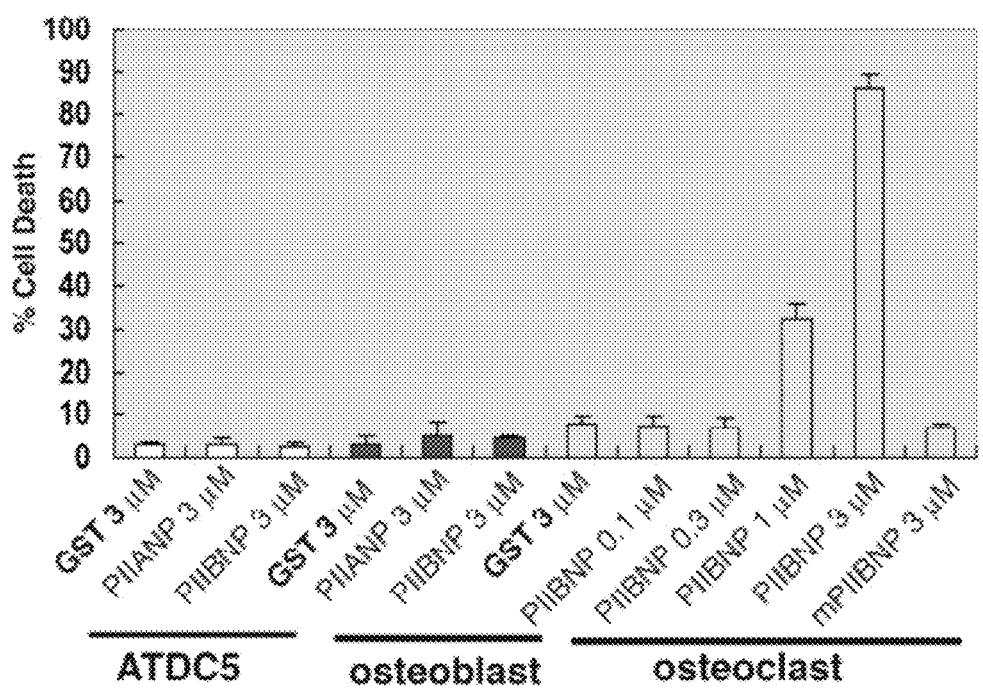
FIG. 10 depicts a graph showing mouse chondrogenic cells (ATDC5), mouse osteoblast cells, and mouse osteoclast cells treated with recombinant GST, PIIBNP or mPIIBNP proteins for 16 hours at 37° C. The cells were trypsinized and cell viability was assayed using a trypan blue exclusion based cell counting. PPIIBNP induced death in osteoclasts that resorb the bone, but not the osteoblasts that form bone. The PIIBNP did not lead to the mouse chondrogenic cell (ATDC5) death because these cells did not express the integrin αv.
Figure 11:
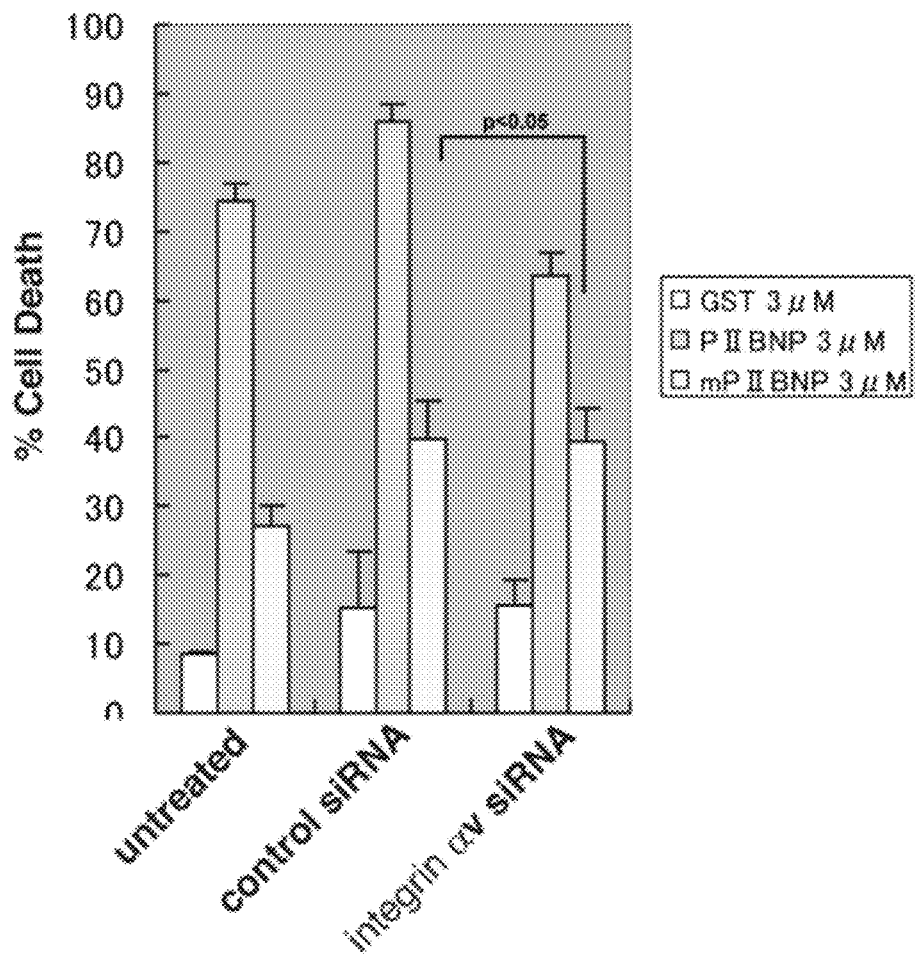
FIG. 11 depicts a graph showing PIIBNP-induced osteoclast death. siRNA specifically targeted to integrin αv was purchased from San Cruz (San Cruz, Calif.). Raw 264.7 cells were differentiated into osteoclasts by treatment with 100 nM of s-RANKL. The integrin αv expression in the osteoblasts were suppressed by treatment of the cells with siRNA. Integrin αv suppressed osteoblasts were incubated with recombinant GST, PIIBNP or mPIIBNP for 16 hours. Cell viability was assayed by a trypan blue exclusion test as described in FIG. 3. PIIBNP-induced osteoclast death was significantly reduced after the cells were treated with integrin αv siRNA compared with the cells treated with control siRNA.

Mouse osteoblast and osteoclast cells were treated with a propeptide of the invention. Type IIB propeptide induced the death of osteoclasts, but not osteoblasts (FIG. 10). The osteoclast death was depending on $\alpha_v$ integrin expression (FIG. 11).

What is claimed is:

1. A method for inhibiting the migration of a cell that expresses an αvβ3 and/or an αvβ5 integrin, the method comprising contacting the cell with an isolated human Type IIB collagen amino propeptide, wherein the propeptide consists of the amino acid sequence encoded by exons 3-8 of the human Type IIB collagen amino propeptide nucleic acid sequence.

2. The method of claim 1, wherein the cell is selected from the group consisting of a tumor cell, an endothelial cell, and an osteoclast cell.

3. The method of claim 2, wherein the tumor cell is selected from the group consisting of a cervical cell, a pancreatic cell, a bone marrow cell, a breast cell, a prostate cell, a skin cell, an ovary cell, a kidney cell, and a lung cell.

4. The method of claim 1, wherein the cell is contacted with an amount of human Type IIB collagen amino propeptide from about 600 nM to about 3.0 μM.

5. The method of claim 1, wherein the cell is further contacted with a therapeutic agent.

* * * * *

SEQUENCE LISTING

<160> NUMBER OF SEQ ID NOS: 12

<210> SEQ ID NO 1
<211> LENGTH: 179
<212> TYPE: PRT
<213> ORGANISM: Homo sapiens

<400> SEQUENCE: 1

Gln Asp Val Gln Glu Ala Gly Ser Cys Val Asp Gln Asp Gly Gln Arg
1               5                   10                  15

Tyr Asn Asp Lys Asp Val Trp Lys Pro Glu Pro Cys Arg Ile Cys Val
            20                  25                  30

Cys Asp Thr Gly Thr Val Leu Cys Asp Asp Ile Ile Cys Glu Asp Val
        35                  40                  45

-continued

```
Lys Asp Cys Leu Ser Pro Glu Ile Pro Leu Gly Glu Cys Cys Pro Ile
    50                  55                  60

Cys Pro Thr Asp Leu Ala Thr Ala Ser Gly Gln Pro Gly Pro Lys Gly
65                  70                  75                  80

Gln Lys Gly Glu Pro Gly Asp Ile Lys Asp Ile Val Gly Pro Lys Gly
                85                  90                  95

Pro Pro Gly Pro Gln Gly Pro Ala Gly Glu Gln Gly Pro Arg Gly Asp
            100                 105                 110

Arg Gly Asp Lys Gly Glu Lys Gly Ala Pro Gly Pro Arg Gly Arg Asp
        115                 120                 125

Gly Glu Pro Gly Thr Pro Gly Asn Pro Gly Pro Gly Pro Pro Gly
    130                 135                 140

Pro Pro Gly Pro Gly Leu Gly Gly Asn Gly Ala Ala Gln Met Ala
145                 150                 155                 160

Gly Gly Phe Asp Glu Lys Ala Gly Gly Ala Gln Leu Gly Val Met Gln
                165                 170                 175

Gly Pro Met

<210> SEQ ID NO 2
<211> LENGTH: 39
<212> TYPE: PRT
<213> ORGANISM: Homo sapiens

<400> SEQUENCE: 2

Gly Pro Lys Gly Pro Pro Gly Pro Gln Gly Pro Ala Gly Glu Gln Gly
1               5                   10                  15

Pro Arg Gly Asp Arg Gly Asp Lys Gly Glu Lys Gly Ala Pro Gly Pro
            20                  25                  30

Arg Gly Arg Asp Gly Glu Pro
        35

<210> SEQ ID NO 3
<211> LENGTH: 39
<212> TYPE: PRT
<213> ORGANISM: Canis familiaris

<400> SEQUENCE: 3

Gly Pro Lys Gly Pro Pro Gly Pro Gln Gly Pro Ala Gly Glu Gln Gly
1               5                   10                  15

Pro Arg Gly Asp Arg Gly Asp Lys Gly Glu Lys Gly Ala Pro Gly Pro
            20                  25                  30

Arg Gly Arg Asp Gly Glu Pro
        35

<210> SEQ ID NO 4
<211> LENGTH: 39
<212> TYPE: PRT
<213> ORGANISM: Equitius doriae

<400> SEQUENCE: 4

Gly Pro Lys Gly Pro Pro Gly Pro Gln Gly Pro Ala Gly Glu Gln Gly
1               5                   10                  15

Pro Arg Gly Asp Arg Gly Asp Lys Gly Glu Lys Gly Ala Pro Gly Pro
            20                  25                  30

Arg Gly Arg Asp Gly Glu Pro
        35

<210> SEQ ID NO 5
```

```
<211> LENGTH: 39
<212> TYPE: PRT
<213> ORGANISM: Rattus rattus

<400> SEQUENCE: 5

Gly Pro Lys Gly Pro Pro Gly Pro Gln Gly Pro Ala Gly Glu Gln Gly
1               5                   10                  15

Pro Arg Gly Asp Arg Gly Asp Lys Gly Glu Arg Gly Ala Pro Gly Pro
                20                  25                  30

Arg Gly Arg Asp Gly Glu Pro
            35

<210> SEQ ID NO 6
<211> LENGTH: 39
<212> TYPE: PRT
<213> ORGANISM: Gallus gallus

<400> SEQUENCE: 6

Gly Pro Arg Gly Pro Pro Gly Pro Gln Gly Pro Ala Gly Glu Gln Gly
1               5                   10                  15

Gln Arg Gly Asp Arg Gly Glu Lys Gly Glu Lys Gly Ala Pro Gly Pro
                20                  25                  30

Arg Gly Arg Asp Gly Glu Pro
            35

<210> SEQ ID NO 7
<211> LENGTH: 39
<212> TYPE: PRT
<213> ORGANISM: Xenopus laevis/gilli

<400> SEQUENCE: 7

Gly Pro Arg Gly Pro Pro Gly Pro Gln Gly Pro Ser Gly Glu Gln Gly
1               5                   10                  15

Ser Arg Gly Glu Arg Gly Asp Lys Gly Glu Lys Gly Ala Pro Gly Pro
                20                  25                  30

Arg Gly Arg Asp Gly Glu Pro
            35

<210> SEQ ID NO 8
<211> LENGTH: 39
<212> TYPE: PRT
<213> ORGANISM: Danio rerio

<400> SEQUENCE: 8

Gly Pro Arg Gly Pro Ala Gly Pro Met Gly Pro Pro Gly Glu Gln Gly
1               5                   10                  15

Thr Arg Gly Glu Arg Gly Ala Lys Gly Glu Lys Gly Ser Pro Gly Pro
                20                  25                  30

Arg Gly Arg Asp Gly Glu Pro
            35

<210> SEQ ID NO 9
<211> LENGTH: 6
<212> TYPE: PRT
<213> ORGANISM: Homo sapiens

<400> SEQUENCE: 9

Arg Gly Asp Arg Gly Asp
1               5

<210> SEQ ID NO 10
<211> LENGTH: 6
```

```
<212> TYPE: PRT
<213> ORGANISM: Homo sapiens

<400> SEQUENCE: 10

Arg Ala Asp Arg Ala Asp
1               5

<210> SEQ ID NO 11
<211> LENGTH: 6
<212> TYPE: PRT
<213> ORGANISM: Homo sapiens

<400> SEQUENCE: 11

Gly Arg Gly Asp Asn Pro
1               5

<210> SEQ ID NO 12
<211> LENGTH: 6
<212> TYPE: PRT
<213> ORGANISM: Homo sapiens

<400> SEQUENCE: 12

Gly Arg Ala Asp Asn Pro
1               5
```